United States Patent
Erdelen et al.

(12)

(10) Patent No.: US 6,251,833 B1
(45) Date of Patent: Jun. 26, 2001

(54) 2-ARYLCYCLOPENTAN-1,3-DIONES

(76) Inventors: Christoph Erdelen; Ulrike Wachendorff-Neumann; Reiner Fischer; Alan Graff; Norbert Mencke; Andreas Turberg, all of c/o Bayer Aktiengesellschaft, D 51368 Leverkusen (DE)

( * ) Notice: Subject to any disclaimer, the term of this patent is extended or adjusted under 35 U.S.C. 154(b) by 0 days.

(21) Appl. No.: 09/380,411

(22) PCT Filed: Feb. 18, 1998

(86) PCT No.: PCT/EP98/00916

§ 371 Date: Aug. 31, 1999

§ 102(e) Date: Aug. 31, 1999

(87) PCT Pub. No.: WO98/39281

PCT Pub. Date: Sep. 11, 1998

(30) Foreign Application Priority Data

Mar. 3, 1997 (DE) .............................. 197 08 607

(51) Int. Cl.$^7$ .................. A01N 35/06; C07C 49/395; C07C 49/297

(52) U.S. Cl. .................. 504/348; 504/307; 504/310; 504/314; 514/478; 514/512; 514/513; 514/520; 514/683; 514/684; 558/70; 558/194; 560/24; 560/29; 560/107; 560/179; 560/205; 560/302; 562/459; 568/309; 568/310; 568/327; 568/328; 568/329; 568/330

(58) Field of Search .................. 504/348, 307, 504/310, 314; 424/301, 304, 331; 568/327, 328, 329, 330, 306, 309, 310; 514/478, 512, 513, 520, 683, 684; 558/70, 194; 560/24, 29, 107, 179, 205, 302; 562/459

(56) References Cited

U.S. PATENT DOCUMENTS

| | | | |
|---|---|---|---|
| 4,283,348 | * 8/1981 | Wheeler | 260/465 D |
| 4,338,122 | 7/1982 | Wheeler | 71/122 |
| 4,436,666 | 3/1984 | Wheeler | 260/455 B |
| 4,526,723 | 7/1985 | Wheeler et al. | 260/410.5 |
| 4,551,547 | * 11/1985 | Wheeler | 560/255 |
| 4,632,698 | 12/1986 | Wheeler | 71/106 |
| 5,808,135 | 9/1998 | Fischer et al. | 560/129 |
| 5,840,661 | 11/1998 | Fischer et al. | 504/348 |

FOREIGN PATENT DOCUMENTS

| | | |
|---|---|---|
| 19518962 | * 1/1996 | (DE) . |
| 94/29268 | 12/1994 | (WO) . |
| 97/01535 | 1/1997 | (WO) . |
| 97/36868 | 10/1997 | (WO) . |

OTHER PUBLICATIONS

Tetrahedron, vol. 48, No. 36, pp. 7519–7526 1992, Micklefield et al Alkylation and Acylation of 5–Phenylsulphonyl– and 5–Cyanobutyrolactones.

J. Chem. Soc. 1967, pp. 405–409, Edwards et al, Constituents of the Higher Fungi. Part LV. Involutin, a Diphenylcyclopenteneone from *Paxillus involutus* (Oeder ex Fries).

Organikium, 15$^{th}$ edition, Berlin (month unavailable) 1977, pp. 499–502, 519–529 and 623, Allgemeine Arbeitsvorschrift für die Äthinylierung von Ketonen.

Chem. Soc.Chem. Commun. 1987, pp. 1228–1230, Chambers et al An Asymmetric Synthesis of Thiotetronic Acids using Chirality Transfer via an Ally Xanthate–to–Dithiocarbonate Rearrangement. X–ray Crystal Structure of (5R)–2, 5–Dihydro–4–Hydroxy–5–mthyl–3–phenyl–5–prop–1'–enyl–2–oxothiphene.

* cited by examiner

Primary Examiner—Sreeni Padmanabhan
(74) Attorney, Agent, or Firm—Joseph C. Gil; Jackie Ann Zurcher

(57) ABSTRACT

The present invention relates to novel 2-aryl-3-hydroxy-$\Delta^2$-cyclopentene-1-one derivatives of the formula (I)

(I)

in which
A, B, $D^1$, $D^2$, G, W, X, Y and Z are each as defined in the description,
to processes for their preparation and to their use as herbicides and pesticides.

17 Claims, No Drawings

2-ARYLCYCLOPENTAN-1,3-DIONES

This is the US National Stage Application of PCT/EP98/00916 filed Feb. 18, 1998.

TECHNICAL FIELD OF THE INVENTION

The present invention relates to novel 2-aryl-3-hydroxy-$\Delta^2$-cyclopentene-1-one derivatives, to processes for their preparation and to their use as herbicides and pesticides.

BACKGROUND OF THE INVENTION

It is known that certain substituted 2-arylcyclopentane diones have herbicidal and acaricidal properties (cf., for example, U.S. Pat. Nos. 4,283,348; 4,338,122; 4,436,666; 4,526,723; 4,551,547, 4,632,698, WO 96/01798 and WO 96/03366). Moreover, compounds which are substituted in a similar manner are known; 3-hydroxy-5,5-dimethyl-2-phenylcyclopent-2-ene-1-one from the publication Micklefield et al., Tetrahedron, (1992), 7519–26 and the natural compound involutin (–)-cis-5-(3,4-dihydroxyphenyl)-3,4-dihydroxy-2-(4-hydroxyphenyl)-cyclopent-2-enone from the publication Edwards et al., J. Chem. Soc. S, (1967), 405–9. An insecticidal or acaricidal action has not been described.

However, the acaricidal and insecticidal activity and/or activity spectrum, and the compatibility of these compounds with plants, in particular crop plants, is not always satisfactory.

DETAILED DESCRIPTION OF THE INVENTION

This invention, accordingly, provides novel compounds of the formula (I)

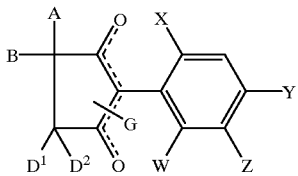

(I)

in which

W represents hydrogen, cyano, nitro, halogen, alkyl, alkenyl, alkinyl, alkoxy, halogenalkyl, halogenalkoxy, in each case optionally substituted phenyl, phenoxy, phenylthio, phenylalkoxy or phenylalkylthio, X represents hydrogen, halogen, alkyl, alkenyl, alkinyl, alkoxy, halogenalkyl, halogenoalkoxy, cyano, nitro, in each case optionally substituted phenyl, phenylalkyl, phenoxy, phenylthio, phenylalkyloxy or phenylalkylthio, with the proviso that at least one of the substituents W and X does not represent hydrogen, Y represents hydrogen, halogen, alkyl, alkoxy, halogenoalkyl, halogenoalkoxy, cyano or nitro, Z represents halogen, alkyl, alkoxy, halogenalkyl, halogenoalkoxy, hydroxyl, cyano, nitro or in each case optionally substituted phenoxy, phenylthio, 5- or 6-membered hetaryloxy, 5- or 6-membered hetarylthio, phenylalkyloxy or phenylalkylthio, or Y and Z together with the carbon atoms to which they are attached represent an optionally substituted ring which is optionally interrupted by one or more heteroatoms, where X and W have one of the meanings mentioned above, or W and Z together with the carbon atoms to which they are attached represent an optionally substituted ring which is optionally interrupted by one or more heteroatoms, where X and Y have one of the meanings mentioned above, A represents hydrogen or represents alkyl, alkenyl, alkinyl, alkoxyalkyl, polyalkoxyalkyl or alkylthioalkyl, each of which is optionally mono- or polysubstituted by identical or different halogens, represents saturated or unsaturated, unsubstituted or substituted cycloalkyl which is optionally interrupted by one or more heteroatoms or represents phenyl or phenylalkyl, each of which is optionally mono- or polysubstituted by identical or different substituents from the group consisting of halogen, alkyl, halogenoalkyl, alkoxy, halogenoalkoxy, cyano and nitro, B represents alkyl or alkoxyalkyl, or A and B together with the carbon atom to which they are attached form a saturated or unsaturated, optionally substituted ring which is optionally interrupted by one or more heteroatoms, or A and B together with the carbon atom to which they are attached form a ring where two substituents together with the carbon atoms to which they are attached form a saturated or unsaturated ring which is optionally mono- or polysubstituted by identical or different substituents from the group consisting of halogen, alkyl and alkoxy and which may contain oxygen or sulphur, $D^1$ and $D^2$ independently of one another each represent hydrogen, halogen, optionally halogen-substituted alkyl or optionally substituted phenyl, G represents hydrogen (a) or represents one of the groups (b)

—CO—$R^1$ (c)

(d)

—$SO_2$—$R^3$ (e)

(f)

 or (g)

E represents a metal ion equivalent or an ammonium ion,

L represents oxygen or sulphur,

M represents oxygen or sulphur, $R^1$ represents alkyl, alkenyl, alkoxyalkyl, alkylthioalkyl or polyalkoxyalkyl, each of which is optionally mono- or polysubstituted by identical or different halogens, or represents optionally substituted, saturated or unsaturated cycloalkyl which may be interrupted by one or more heteroatoms, or represents in each case optionally substituted phenyl, phenylalkyl, hetaryl, phenoxyalkyl or hetaryloxyalkyl, R² represents alkyl, alkenyl, alkoxyalkyl, polyalkoxyalkyl, each of which is optionally mono- or polysubstituted by identical or different halogens, or represents in each case optionally substituted cycloalkyl, phenyl or benzyl, R³ represents alkyl which is optionally mono- or polysubstituted by identical or different halogens or represents in each case optionally substituted phenyl or phenylalkyl, R⁴ and R⁵ independently of one another each represent alkyl, alkoxy, alkylamino, alkenylamino, dialkylamino, dialkenylamino, alkylthio, alkenylthio, alkinylthio, cycloalkylthio, each of which is optionally mono- or polysubstituted by identical or different halogens, or represents in each case optionally substituted phenyl, phenoxy or phenylthio, R⁶ and R⁷ independently of one another each represent hydrogen, represent alkyl, cycloalkyl, alkenyl, alkoxy, alkoxyalkyl, each of which is optionally mono- or polysubstituted by identical or different halogens, or represent optionally substituted phenyl or optionally substituted benzyl, or together with the N atom to which they are attached form an optionally substituted ring which optionally contains oxygen or sulphur, and the enantiomerically pure forms of compounds of the formula (I).

Depending, inter alia, on the nature of the substituents, the compounds of the formula (I) can be present as geometrical and/or optical isomers or isomer mixtures of different composition which are separated, if appropriate, in a customary manner by physical methods, for example by chromatographic methods.

Depending on the position of the substituent G, the compounds of the formula (I) can be present in the two isomeric forms of the formulae I-A and -B (I-A)

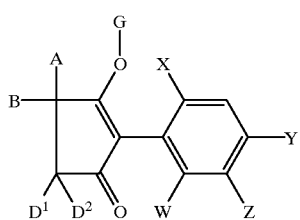

(I-B)

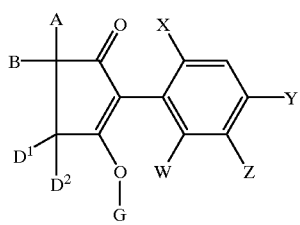

which is meant to be expressed by the dotted line in the formula (I).

The compounds of the formulae I-A and I-B can be present both as mixtures and in the form of their pure isomers. Mixtures of the compounds of the formulae I-A and I-B may optionally be separated by physical methods, for example by chromatographic methods.

For reasons of clarity, hereinbelow only one of the possible isomers is shown in each case. It is implied that the compound in question may be present as a mixture of isomers or in the respective other isomeric form.

Including the various meanings (a), (b), (c), (d), (e), (f) and (g) of the group G, the following principal structures (Ia) to (Ig) result:

(Ia)

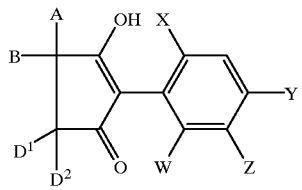

(Ib)

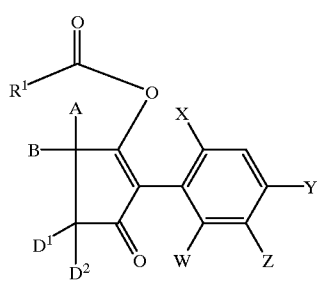

(Ic)

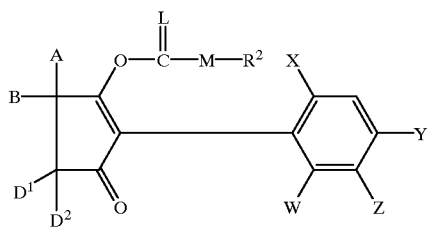

(Id)

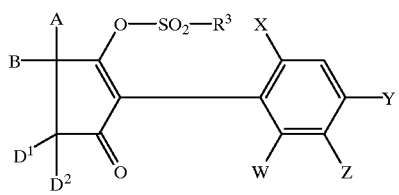

(Ie)

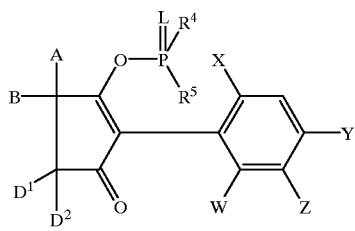

(If)

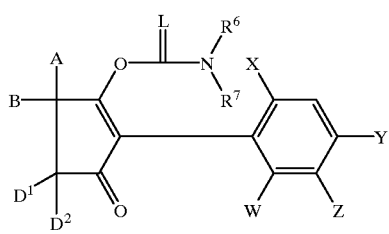

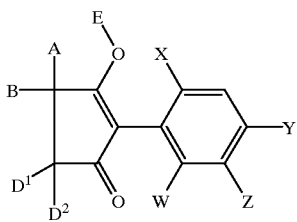

(Ig)

in which
A, B, D$^1$, D$^2$, E, L, M, W, X, Y, Z, R$^1$, R$^2$, R$^3$, R$^4$, R$^5$, R$^6$ and R$^7$ are each as defined above.

Furthermore, it has been found
(A) that compounds of the formula (IA)

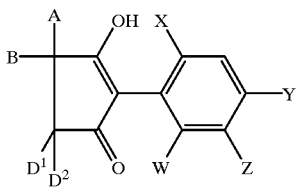

(Ia)

in which
A, B, D$^1$, D$^2$, W, X, Y and Z are each as defined above are obtained when
ketocarboxylic esters of the formula (II)

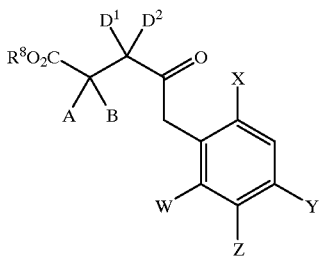

(II)

in which
A, B, D$^1$, D$^2$, W, X, Y and Z are each as defined above and R$^8$ represents alkyl (in particular C$_1$–C$_8$-alkyl)
are cyclized intramolecularly, if appropriate in the presence of a diluent and in the presence of a base, and
(B) that the compounds of the formula (Ib) shown above, in which A, B, D$^1$, D$^2$, R$^1$, W, X, Y and Z are each as defined above, are obtained when compounds of the formula (Ia) shown above, in which A, B, D$^1$, D$^2$, W, X, Y and Z are each as defined above are reacted
α) with acyl halides of the formula (III)

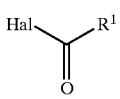

(III)

in which
R$^1$ is as defined above and
Hal represents halogen (in particular chlorine or bromine)

or
β) with carboxylic anhydrides of the formula (IV)

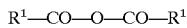

R$^1$—CO—O—CO—R$^1$ (IV)

in which
R$^1$ is as defined above,
if appropriate in the presence of a diluent and if appropriate in the presence of an acid binder;
(C) that the compounds of the formula (Ic) shown above, in which A, B, D$^1$, D$^2$, R$^2$, W, M, X, Y and Z are each as defined above and L represents oxygen, are obtained when compounds of the formula (Ia) shown above, in which A, B, D$^1$, D$^2$, W, X, Y and Z are each as defined above, are reacted with chloroformic esters or chloroformic thioesters of the formula (V)

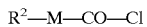

R$^2$—M—CO—Cl (V)

in which
R$^2$ and M are each as defined above,
if appropriate in the presence of a diluent and if appropriate in the presence of an acid binder;
(D) that compounds of the formula (Ic) shown above, in which A, B, D$^1$, D$^2$, R$^2$, W, M, X, Y and Z are each as defined above and L represents sulphur, are obtained when compounds of the formula (la) shown above, in which A, B, D$^1$, D$^2$, W, X, Y and Z are each as defined above, are reacted with chloromonothioformic esters or chlordithioformic esters of the formula (VI)

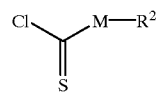

(VI)

in which
M and R$^2$ are each as defined above,
if appropriate in the presence of a diluent and if appropriate in the presence of an acid binder, or (E) that compounds of the formula (Id) shown above, in which A, B, D$^1$, D$^2$, R$^3$, W, X, Y and Z are each as defined above, are obtained when compounds of the formula (Ia) shown above, in which A, B, D$^1$, D$^2$, W, X, Y and Z are each as defined above, are reacted with sulphonyl chlorides of the formula (VII)

R$^3$—SO$_2$—Cl (VII)

in which
R$^3$ is as defined above,
if appropriate in the presence of a diluent and if appropriate in the presence of an acid binder,
(F) that compounds of the formula (Ie) shown above, in which A, B, D$^1$, D$^2$, L, R$^4$, R$^5$, W, X, Y and Z are each as defined above, are obtained when compounds of the formula (Ia) shown above, in which A, B, D¹, D², W, X, Y and Z are each as defined above, are reacted with phosphorus compounds of the formula (VIII)

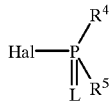
(VIII)

in which

L, R⁴ and R⁵ are each as defined above and

Hal represents halogen (in particular chlorine or bromine), if appropriate in the presence of a diluent and if appropriate in the presence of an acid binder, (G) that compounds of the formula (I1) shown above, in which A, B, D¹, D², L, R⁶, R⁷, W, X, Y and Z are each as defined above, are obtained when compounds of the formula (Ia) shown above, in which A, B, D¹, D², W, X, Y and Z are each as defined above, are in each case reacted α) with isocyanates or isothiocyanates of the formula (XI)

R⁶—N=C=L (XI)

in which

R⁶ and L are each as defined above, if appropriate in the presence of a diluent and if appropriate in the presence of a catalyst, or β) with carbamoyl chlorides or thiocarbamoyl chlorides of the formula (XII)

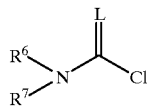
(XII)

in which

L, R⁶ and R⁷ are each as defined above, if appropriate in the presence of a diluent and if appropriate in the presence of an acid binder, (H) that compounds of the formula (Ig) shown above, in which A, B, D¹, D², E, W, X, Y and Z are each as defined above, are obtained when compounds of the formula (Ia), in which A, B, D¹, D², W, X, Y and Z are each as defined above, are reacted with metal compounds or amines of the formula (IX) or (X)

Me(OR¹⁰)ₜ (IX)

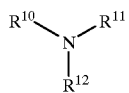
(X)

in which

Me represents a mono- or divalent metal (preferably an alkali metal or alkaline earth metal such as lithium, sodium, potassium, magnesium or calcium), t represents the number 1 or 2 and R¹⁰, R¹¹, R¹² independently of one another each represent hydrogen or alkyl (preferably $C_1$–$C_8$-alkyl), if appropriate in the presence of a diluent.

Furthermore, it has been found that the novel compounds of the formula (I) have very good activity as pesticides, preferably as insecticides and acaricides and, at higher application rates, also as herbicides and are additionally tolerated very well by plants, in particular by crop plants.

The formula (I) provides a general definition of the compounds according to the invention. Preferred substituents or ranges of the radicals listed in the formulae mentioned hereinabove and hereinbelow are illustrated below:

W preferably represents hydrogen, halogen, $C_1$–$C_6$-alkyl, $C_2$–$C_6$-alkenyl or $C_2$–$C_6$-alkinyl, $C_1$–$C_6$-alkoxy, $C_1$–$C_4$-halogenoalkyl, $C_1$–$C_4$-halogenoalkoxy, nitro, cyano or m each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenoxy, phenylthio, phenyl-$C_1$–$C_4$-alkoxy or phenyl-$C_1$–$C_4$-alkylthio, X preferably represents hydrogen, halogen, $C_1$–$C_6$-alkyl, $C_2$–$C_6$-alkenyl, $C_2$–$C_6$-alkinyl, $C_1$–$C_6$-alkoxy, $C_1$–$C_4$-halogenoalkyl, $C_1$–$C_4$-halogenoalkoxy, cyano, nitro or in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenyl-$C_1$–$C_4$-alkyl, phenoxy, phenylthio, phenyl-$C_1$–$C_4$-alkoxy or phenyl-$C_1$–$C_4$-alkylthio, with the proviso that at least one of the substituents W and X does not represent hydrogen.

Y preferably represents hydrogen, halogen, $C_1$–$C_6$-alkyl, $C_1$–$C_6$-alkoxy, $C_1$–$C_4$-halogenoalkyl, $C_1$–$C_4$-halogenoalkoxy, cyano or nitro.

Z preferably represents halogen, $C_1$–$C_6$-alkyl, $C_1$–$C_6$-alkoxy, $C_1$–$C_4$-halogenoalkyl, $C_1$–$C_4$-halogenoalkoxy, hydroxyl, cyano, nitro or in each case optionally halogen-, $C_1$–$C_4$-alkyl-, $C_1$–$C_4$-alkoxy-, $C_1$–$C_4$-halogenoalkyl-, $C_1$–$C_4$-halogenoalkoxy-, nitro- or cyano- substituted phenoxy, phenylthio, thiazolyloxy, pyridinyloxy, pyrimidinyloxy, pyrazolyloxy, phenyl-$C_1$–$C_4$-alkyloxy or phenyl-$C_1$–$C_4$-alkylthio, or Y and Z together preferably represent in each case optionally halogen-, $C_1$–$C_6$-alkyl-, $C_1$–$C_6$-alkoxy- or $C_1$–$C_4$-halogenoalkyl-substituted $C_3$–$C_5$-alkanediyl or $C_3$–$C_5$-alkenediyl in which optionally one to three members may be replaced independently of one another by oxygen, sulphur, nitrogen or a carbonyl group, where X and W have one of the meanings mentioned above, or W and Z together preferably represent in each case optionally halogen-, $C_1$–$C_6$-alkyl-, $C_1$–$C_6$-alkoxy- or $C_1$–$C_4$-halogenoalkyl-substituted $C_3$–$C_5$-alkanediyl or $C_3$–$C_5$-alkenediyl in which optionally one to three members may be replaced independently of one another by oxygen, sulphur, nitrogen or a carbonyl group, where X and Y have one of the meanings mentioned above.

A preferably represents hydrogen, represents in each case optionally halogen-substituted $C_1$–$C_{12}$-alkyl, $C_3$–$C_8$-alkenyl, $C_1$–$C_{10}$-alkoxy-$C_1$–$C_8$-alkyl, poly-$C_1$–$C_8$-alkoxy-$C_1$–$C_8$-alkyl or $C_1$–$C_{10}$-alkylthio-$C_1$–$C_6$-alkyl, represents in each case optionally halogen-, $C_1$–$C_6$-alkyl- or $C_1$–$C_6$-alkoxy-substituted $C_3$–$C_8$-cycloalkyl in which optionally one or two not directly adjacent methylene groups are replaced by oxygen and/or sulphur or represents in each case optionally halogen-, $C_1$–$C_6$-alkyl/$C_1$–$C_6$-halogenoalkyl-, $C_1$–$C_6$-alkoxy-, $C_1$–$C_6$-halogenoalkoxy-, cyano- or nitro-substituted phenyl or phenyl-$C_1$–$C_6$-alkyl.

B preferably represents $C_1$–$C_{12}$-alkyl or $C_1$–$C_8$-alkoxy-$C_1$–$C_6$-alkyl or A, B and the carbon atom to which they are attached preferably represent $C_3$–$C_{10}$-cycloalkyl or $C_5$–$C_{10}$- cycloalkenyl in which optionally one methylene group is replaced by oxygen or sulphur and which are optionally substituted by $C_1-C_8$-alkyl, $C_3-C_{10}$-cycloalkyl, $C_1-C_8$-halogenoalkyl, $C_1-C_8$-alkoxy, $C_1-C_8$-alkylthio, halogen or phenyl, or A, B and the carbon atom to which they are attached preferably represent $C_5-C_6$-cycloalkyl which is optionally substituted by an alkylenediyl or by an alkylenedioxyl or by an alkylenedithioyl group which optionally contains one or two not directly adjacent oxygen and/or sulphur atoms which, with the carbon atom to which it is attached, forms a further five- to eight-membered ring, or A, B and the carbon atom to which they are attached preferably represent $C_3-C_8$cycloalkyl or $C_5-C_8$-cycloalkenyl in which two carbon atoms are linked with one another by $C_3-C_6$-alkanediyl, $C_3-C_6$-alkenediyl or $C_4-C_6$-alkanediendiyl, each of which is optionally substituted by $C_1-C_6$-alkyl, $C_1-C_6$-alkoxy or halogen, in which in each case optionally one methylene group is replaced by oxygen or sulphur.

$D^1$ and $D^2$ independently of one another each preferably represent hydrogen, halogen, $C_1-C_6$-alkyl which is optionally mono- or polysubstituted by identical or different halogens or represent phenyl which is optionally mono- or polysubstituted by identical or different substituents from the group consisting of halogen, $C_1-C_6$-alkyl, $C_1-C_6$-alkoxy, nitro, $C_1-C_6$-halogenoalkyl or $C_1-C_6$-halogenoalkoxy.

G preferably represents hydrogen (a) or represents one of the groups (b)
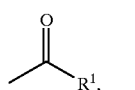

(c)
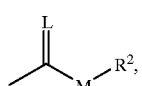

(d)
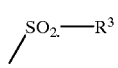

(e)
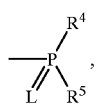

(f)
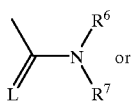

(g)
E, in which
  E represents a metal ion equivalent or an ammonium ion,
  L represents oxygen or sulphur and
  M represents oxygen or sulphur.

$R^1$ preferably represents in each case optionally halogen-substituted $C_1-C_{20}$-alkyl, $C_2-C_{20}$-alkenyl, $C_1-C_8$-alkoxy-$C_1-C_8$-alkyl, $C_1-C_8$-alkylthio-$C_1-C_8$-alkyl or poly-$C_1-C_8$-alkoxy-$C_1-C_8$-alkyl or represents optionally halogen-, $C_1-C_6$-alkyl- or $C_1-C_6$-alkoxy-substituted $C_3-C_8$-cycloalkyl in which optionally one or two not directly adjacent methylene groups are replaced by oxygen and/or sulphur, represents optionally halogen-, cyano-, nitro-, $C_1-C_6$-alkyl-, $C_1-C_6$-alkoxy-, $C_1-C_6$-halogenoalkyl-, $C_1-C_6$-halogenoalkoxy-, $C_1-C_6$-alkylthio- or $C_1-C_6$-alkylsulphonyl-substituted phenyl, represents optionally halogen-, nitro, cyano, $C_1-C_6$-alkyl, $C_1-C_6$-alkoxy, $C_1-C_6$-halogenoalkyl- or $C_1-C_6$-halogenoalkoxy-substituted phenyl-$C_1-C_6$-alkyl, represents optionally halogen- or $C_1-C_6$-alkyl-substituted 5- or 6-membered hetaryl having one or two heteroatoms from the group consisting of oxygen, sulphur and nitrogen, for example pyrazolyl, thiazolyl, pyridyl, pyrimidyl, furanyl or thienyl, represents optionally halogen- or $C_1-C_6$-alkyl-substituted phenoxy-$C_1-C_6$-alkyl or represents optionally halogen-, amino- or $C_1-C_6$-alkyl-substituted 5- or 6-membered hetaryloxy-$C_1-C_6$-alkyl having one or two heteroatoms from the group consisting of oxygen, sulphur and nitrogen, for example pyridyloxy-$C_1-C_6$-alkyl, pyrimidyloxy-$C_1-C_6$-alkyly or thiazolyloxy-$C_1-C_6$-alkyl.

$R^2$ preferably represents in each case optionally halogen-substituted $C_1-C_{20}$-alkyl, $C_2-C_{20}$-alkenyl, $C_1-C_8$-alkoxy-$C_2-C_8$-alkyl or poly-$C_1-C_8$-alkoxy-$C_2-C_8$-alkyl, represents optionally halogen-, $C_1-C_6$-alkyl- or $C_1-C_6$-alkoxy-substituted $C_3-C_8$-cycloalkyl or represents in each case optionally halogen-, cyano-, nitro-, $C_1-C_6$-alkyl-, $C_1-C_6$-alkoxy-, $C_1-C_6$-halogenoalkyl- or $C_1-C_6$-halogenoalkoxy-substituted phenyl or benzyl.

$R^3$ preferably represents optionally halogen-substituted $C_1-C_8$-alkyl or in each case optionally halogen-, $C_1-C_6$-alkyl-, $C_1-C_6$-alkoxy-, $C_1-C_4$-halogenoalkyl-, $C_1-C_4$-halogenoalkoxy-, cyano- or nitro-substituted phenyl or benzyl.

$R^4$ and $R^5$ independently of one another each preferably represent in each case optionally halogen-substituted $C_1-C_8$-alkyl, $C_1-C_8$-alkoxy, $C_1-C_8$-alkylamino, di-($C_1-C_8$-alkyl)amino, $C_1-C_8$-alkylthio or $C_3-C_8$-alkenylthio or represent in each case optionally halogen-, nitro-, cyano-, $C_1-C_4$-alkoxy-, $C_1-C_4$-halogenoalkoxy-, $C_1-C_4$-alkylthio-, $C_1-C_4$-halogenoalkylthio, $C_1-C_4$-alkyl- or $C_1-C_4$-halogenoalkyl-substituted phenyl, phenoxy or phenylthio.

$R^6$ and $R^7$ independently of one another each preferably represent hydrogen, represent in each case optionally halogen-substituted $C_1-C_8$-alkyl, $C_3-C_8$-cycloalkyl, $C_1-C_8$-alkoxy, $C_3-C_8$-alkenyl or $C_1-C_8$-alkoxy-$C_2-C_8$-alkyl, represent in each case optionally halogen-, $C_1-C_8$-alkyl-, $C_1-C_8$-halogenoalkyl- or $C_1-C_8$-alkoxy-substituted phenyl or benzyl or together represent an optionally $C_1-C_6$-alkyl-substituted $C_3-C_6$-alkylene radical in which optionally one methylene group is replaced by oxygen or sulphur.

W particularly preferably represents hydrogen, fluorine, chlorine, bromine, $C_1-C_4$-alkyl, $C_1-C_4$-alkoxy, $C_1-C_2$-halogenoalkyl, $C_1-C_2$-halogenoalkoxy, nitro, cyano or in each case optionally fluorine-, chlorine-, bromine-, $C_1-C_4$-alkyl-, $C_1-C_4$-alkoxy-, $C_1-C_2$-halogenoalkyl-, $C_1-C_2$-halogenoalkoxy-, nitro- or cyano-substituted phenyl, phenoxy or benzyloxy.

X particularly preferably represents hydrogen, fluorine, chlorine, bromine, $C_1-C_4$-alkyl, $C_1-C_4$-alkoxy, $C_1-C_2$-halogenoalkyl, $C_1-C_2$-halogenoalkoxy, cyano, nitro or in each case optionally fluorine-, chlorine-, bromine-, $C_1-C_4$-alkyl-, $C_1-C_4$-alkoxy-, $C_1-C_2$-halogenoalkyl-, $C_1-C_2$-halogenoalkoxy-, nitro- or cyano-substituted phenyl, phenoxy, benzyl or benzyloxy, with the proviso that at least one of the substituents W and X does not represent hydrogen.

Y particularly preferably represents hydrogen, fluorine, chlorine, bromine $C_1$–$C_4$-alkyl, $C_1$–$C_4$-alkoxy, $C_1$–$C_2$-halogenoalkyl, $C_1$–$C_2$-halogenoalkoxy, cyano or nitro.

Z particularly preferably represents fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, hydroxyl, cyano, nitro or in each case optionally fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy-, nitro- or cyano-substituted phenoxy or benzyloxy, or Y and Z together particularly preferably represent optionally fluorine-, chlorine-, bromine-, $C_1$–$C_4$-alkyl-, $C_1$–$C_4$-alkoxy- or $C_1$–$C_2$-halogenoalkyl-substituted $C_3C_4$-alkanediyl in which optionally one or two not directly adjacent members may be replaced independently of one another by oxygen, sulphur or nitrogen, or represent $C_3$–$C_4$-alkenediyl in which optionally one member is replaced by oxygen, sulphur or nitrogen, where X and W have one of the meanings mentioned above, or W and Z together particularly preferably represent in each case optionally fluorine-, chlorine-, bromine-, $C_1$–$C_4$-alkyl-, $C_1$–$C_4$-alkoxy- or $C_1$–$C_2$-halogenoalkyl-substituted $C_3$–$C_4$-alkanediyl in which one or two not directly adjacent members may be replaced independently of one another by oxygen, sulphur or nitrogen, or represent $C_3$–$C_4$-alkenediyl in which optionally one member is replaced by oxygen, sulphur or nitrogen, where X and Y have one of the meanings mentioned above.

A particularly preferably represents hydrogen, represents in each case optionally fluorine- or chlorine-substituted $C_1$–$C_{10}$-alkyl, $C_3$–$C_6$-alkenyl, $C_1$–$C_8$-alkoxy-$C_1$–$C_6$-alkyl, poly-$C_1$–$C_6$-alkoxy-$C_1$–$C_6$-alkyl or $C_1$–$C_8$-alkylthio-$C_1$–$C_6$-alkyl or represent optionally fluorine-, chlorine-, $C_1$–$C_4$-alkyl- or $C_1$–$C_4$-alkoxy-substituted $C_3$–$C_7$-cycloalkyl in which optionally one or two not directly adjacent methylene groups are replaced by oxygen and/or sulphur or represent in each case optionally fluorine-, chlorine-, bromine-, $C_1$–$C_4$-alkyl-, $C_1$–$C_4$-halogenoalkyl-, $C_1$–$C_4$-alkoxy-, $C_1$–$C_4$-halogenoalkoxy-, cyano- or nitro-substituted phenyl or phenyl-$C_1$–$C_4$-alkyl, B particularly preferably represents $C_1$–$C_{10}$-alkyl or $C_1$–$C_6$-alkoxy-$C_1$–$C_4$-alkyl or A, B and the carbon atom to which they are attached particularly preferably represent $C_3$–$C_8$-cycloalkyl or $C_5$–$C_8$-cycloalkenyl in which in each case optionally one methylene group is replaced by oxygen or sulphur and which are optionally substituted by $C_1$–$C_6$-alkyl, $C_3$–$C_8$-cycloalkyl, $C_1$–$C_3$-halogenoalkyl, $C_1$–$C_6$-alkoxy, $C_1$–$C_6$-alkylthio, fluorine, chlorine or phenyl, or A, B and the carbon atom to which they are attached particularly preferably represent $C_5$–$C_6$-cycloalkyl which is substituted by an alkylenediyl or by an alkylenedioxyl or by an alkylenedithio group group which optionally contains one or two not directly adjacent oxygen or sulphur atoms which, with the carbon atom to which it is attached, forms a further five- to seven-membered ring, or A, B and the carbon atom to which they are attached particularly preferably represent $C_3$–$C_6$-cycloalkyl or $C_5$–$C_6$-cycloalkenyl in which two carbon atoms are linked by in each case optionally $C_1$–$C_4$-alkyl-, $C_1$–$C_4$-alkoxy-, fluorine-, chlorine- or bromine-substituted $C_3$–$C_5$-alkanediyl, $C_3$–$C_5$-alkenediyl, where in each case optionally one methylene group is replaced by oxygen or sulphur, or by butadienediyl.

$D^1$ and $D^2$ independently of one another each preferably represent hydrogen or particularly preferably represent $C_1$–$C_4$-alkyl which is optionally mono- to pentasubstituted by identical or different substituents from the group consisting of fluorine and chlorine.

G particularly preferably represents hydrogen (a) or represents one of the groups

(b)

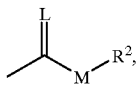

(c)

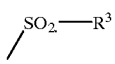

(d)

(e)

(f)

or

E, (g)

in which
E represents a metal ion equivalent or an ammonium ion,
L represents oxygen or sulphur and
M represents oxygen or sulphur.

$R^1$ particularly represents in each case optionally fluorine- or chlorine-substituted $C_1$–$C_{16}$-alkyl, $C_2$–$C_{16}$-alkenyl, $C_1$–$C_6$-alkoxy-$C_1$–$C_6$-alkyl, $C_1$–$C_6$alkylthio-$C_1$–$C_6$-alkyl or poly-$C_1$–$C_6$-alkoxy-$C_1$–$C_6$-alkyl or represents optionally fluorine-, chlorine- $C_1$–$C_5$-alkyl- or $C_1$–$C_5$-alkoxy-substituted $C_3$–$C_7$-cycloalkyl in which optionally one or two not directly adjacent methylene groups are replaced by oxygen and/or sulphur, represents optionally fluorine-, chlorine-, bromine-, cyano-, nitro-, $C_1$–$C_4$-alkyl-, $C_1$–$C_4$-alkoxy-, $C_1$–$C_3$-halogenoalkyl-, $C_1$–$C_3$-halogenoalkoxy-, $C_1$–$C_4$-alkylthio- or $C_1$–$C_4$-alkylsulphonyl-substituted phenyl, represents optionally fluorine-, chlorine-, bromine-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl-$C_1$–$C_4$-alkyl, represents in each case optionally fluorine-, chlorine- bromine- or $C_1$–$C_4$-alkyl-substituted pyrazolyl, thiazolyl, pyridyl, pyrimidyl, furanyl or thienyl, represents optionally fluorine-, chlorine-, bromine- or $C_1$–$C_4$-alkyl-substituted phenoxy-$C_1$–$C_5$-alkyl or represents in each case optionally fluorine-, chlorine-, bromine-, amino- or $C_1$–$C_4$-alkyl-substituted pyridyloxy-$C_1$–$C_5$-alkyl, pyrimidyloxy-$C_1$–$C_5$-alkyl or thiazolyloxy-$C_1$–$C_5$-alkyl.

$R^2$ particularly preferably represents in each case optionally fluorine- or chlorine-substituted $C_1$–$C_{16}$-alkyl, $C_2$–$C_{16}$-alkenyl, $C_1$–$C_6$-alkoxy-$C_2$–$C_6$-alkyl or poly-$C_1$–$C_6$-alkoxy-$C_2$–$C_6$-alkyl, represents optionally fluorine-, chlorine-, $C_1$–$C_4$-alkyl- or $C_1$–$C_4$alkoxy-substituted $C_3$–$C_7$-cycloalkyl or represents in each case optionally fluorine-, chlorine-, bromine-, cyano-, nitro-, $C_1$–$C_4$-alkyl-, $C_1$–$C_3$-alkoxy-, $C_1$–$C_3$-halogenoalkyl- or $C_1$–$C_3$-halogenoalkoxy-substituted phenyl or benzyl.

$R^3$ particularly preferably represents optionally fluorine- or chlorine-substituted $C_1$–$C_6$-alkyl or represents in each case optionally fluorine-, chlorine-, bromine-, $C_1$–$C_4$-alkyl-, $C_1$–$C_4$-alkoxy-, $C_1$–$C_2$-halogenoalkoxy-, $C_1$–$C_2$-halogenoalkyl-, cyano or nitro-substituted phenyl or benzyl.

$R^4$ and $R^5$ independently of one another each particularly preferably represent in each case optionally fluorine- or chlorine-substituted $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio or $C_3$–$C_4$-alkenylthio or represent in each case optionally fluorine-, chlorine-, bromine-, nitro-, cyano-, $C_1$–$C_3$-alkoxy-, $C_1$–$C_3$-halogenoalkoxy-, $C_1$–$C_3$-alkylthio-, $C_1$–$C_3$-halogenoalkylthio-, $C_1$–$C_3$-alkyl- or $C_1$–$C_3$-halogenoalkyl-substituted phenyl, phenoxy or phenylthio.

$R^6$ and $R^7$ independently of one another each particularly preferably represent hydrogen, represent in each case optionally fluorine- or chlorine-substituted $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, represent in each case optionally fluorine-, chlorine-, bromine-, $C_1$–$C_5$-halogenoalkyl-, $C_1$–$C_5$-alkyl- or $C_1$–$C_5$-alkoxy-substituted phenyl or benzyl, or together represent an optionally $C_1$–$C_4$-alkyl-substituted $C_3$–$C_6$-alkylene radical in which optionally one methylene group is replaced by oxygen or sulphur.

W very particularly preferably represents hydrogen, fluorine, chlorine, bromine, methyl, ethyl, n-propyl, n-butyl, iso-propyl, iso-butyl, tert-butyl, methoxy, ethoxy, n-propoxy, iso-propoxy, trifluoromethyl, difluoromethoxy, trifluoromethoxy, cyano, nitro, phenyl or benzyloxy.

X very particularly preferably represents hydrogen, fluorine, chlorine, bromine, methyl, ethyl, n-propyl, n-butyl, iso-butyl, iso-propyl, tert-butyl, methoxy, ethoxy, n-propoxy, iso-propoxy, trifluoromethyl, trifluoromethoxy, difluoromethoxy, cyano, nitro, phenyl or benzyloxy, with the proviso that at least one of the substituents W and X does not represent hydrogen.

Y very particularly preferably represents hydrogen, fluorine, chlorine, bromine, methyl, ethyl, n-propyl, iso-propyl, n-butyl, iso-butyl, tert-butyl, methoxy, ethoxy, n-propoxy, iso-propoxy, trifluoromethyl, trifluoromethoxy, difluoromethoxy, cyano or nitro, Z very particularly preferably represents fluorine, chlorine, bromine, methyl, ethyl, n-propyl, n-butyl, iso-butyl, iso-propyl, tert-butyl, methoxy, ethoxy, n-propoxy, iso-propoxy, trifluoromethyl, trifluoromethoxy, difluoromethoxy, cyano or nitro, or Y and Z together very particularly preferably represent optionally fluorine-, chlorine-, methyl-, ethyl-, n-propyl-, iso-propyl-, methoxy-, ethoxy-, n-propoxy-, iso-propoxy- or trifluoromethyl-substituted $C_3$–$C_4$-alkanediyl in which optionally two not directly adjacent members are replaced by oxygen, where W and X have one of the meanings mentioned above, or W and Z together very particularly preferably represent optionally fluorine-, chlorine-, methyl-, ethyl-, n-propyl-, iso-propyl-, methoxy-, ethoxy-, n-propoxy-, iso-propoxy- or trifluoromethyl-substituted $C_3$–$C_4$-alkanediyl in which optionally two not directly adjacent members are replaced by oxygen, where X and Y have one of the meanings mentioned above.

A very particularly preferably represents hydrogen, represents in each case optionally fluorine- or chlorine-substituted $C_1$–$C_8$-alkyl, $C_3$–$C_4$-alkenyl, $C_1$–$C_6$-alkoxy-$C_1$–$C_4$-alkyl, poly-$C_1$–$C_4$-alkoxy-$C_1$–$C_4$-alkyl or $C_1$–$C_6$-alkylthio-$C_1$–$C_4$-alkyl or represents optionally fluorine-, chlorine-, methyl- or methoxy-substituted $C_3$–$C_6$-cycloalkyl in which optionally one or two not directly adjacent methylene groups are replaced by oxygen and/or sulphur or represents in each case optionally fluorine-, chlorine-, bromine-, methyl-, ethyl-, n-propyl-, iso-propyl-, methoxy-, ethoxy-, trifluoromethyl-, trifluoromethoxy-, cyano- or nitro-substituted phenyl or benzyl.

B very particularly preferably represents $C_1$–$C_8$-alkyl or $C_1$–$C_4$-alkoxy-$C_1$–$C_2$-alkyl or A, B and the carbon atom to which they are attached very particularly preferably represent $C_3$–$C_8$-cycloalkyl or $C_5$–$C_8$-cycloalkenyl in which in each case optionally one methylene group is replaced by oxygen or sulphur and which are optionally substituted by methyl, ethyl, n-propyl, iso-propyl, n-butyl, iso-butyl, sec-butyl, tert-butyl, cyclohexyl, trifluoromethyl, methoxy, ethoxy, n-propoxy, iso-propoxy, n-butoxy, iso-butoxy, sec-butoxy, tert-butoxy, methylthio, ethylthio, fluorine, chlorine or phenyl.

$D^1$ and $D^2$ independently of one another each very particularly preferably represent hydrogen, methyl or ethyl.

G very particularly preferably represents hydrogen (a) or represents one of the groups

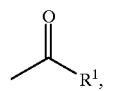

(b)

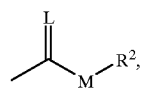

(c)

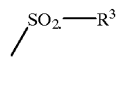

(d)

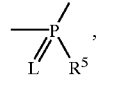

(e)

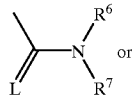

(f)

E, (g)

in which

E represents a metal ion equivalent or an ammonium ion,

L represents oxygen or sulphur and

M represents oxygen or sulphur.

$R^1$ very particularly preferably represents in each case optionally fluorine- or chlorine-substituted $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl or poly-$C_1$–$C_4$-alkoxy-$C_1$–$C_4$-alkyl or represents optionally fluorine-, chlorine-, methyl-, ethyl-, n-propyl-, i-propyl-, n-butyl-, i-butyl-, tert-butyl-, methoxy-, ethoxy-, n-propoxy- or iso-propoxy-substituted $C_3$–$C_6$-cycloalkyl in which optionally one or two not directly adjacent methylene groups are replaced by oxygen and/or sulphur, represents optionally fluorine-, chlorine-, bromine-, cyano-, nitro-, methyl-, ethyl-, n-propyl-, i-propyl-, methoxy-, ethoxy-, trifluoromethyl-, trifluoromethoxy-, methylthio-, ethylthio-, methylsulphonyl- or ethylsulphonyl-substituted phenyl, represents optionally fluorine-, chlorine-, bromine-, methyl-, ethyl-, n-propyl-, i-propyl-, methoxy-, ethoxy-, trifluoromethyl- or trifluoromethoxy-substituted benzyl, represents in each case optionally fluorine-, chlorine-, bromine-, methyl- or ethyl-substituted furanyl, thienyl or pyridyl, represents optionally fluorine-, chlorine-, methyl- or ethyl-substituted phenoxy-$C_1$–$C_4$-alkyl or represents in each case optionally fluorine-, chlorine-, amino-, methyl- or ethyl-substituted pyridyloxy-$C_1$–$C_4$-alkyl, pyrimidyloxy-$C_1$–$C_4$-alkyl or thiazolyloxy-$C_1$–$C_4$-alkyl.

$R^2$ very particularly preferably represents in each case optionally fluorine- or chlorine-substituted $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, represents optionally fluorine-, chlorine-, methyl-, ethyl-, n-propyl-, iso-propyl- or methoxy-substituted $C_3$–$C_6$-cycloalkyl, or represents in each case optionally fluorine-, chlorine-, cyano- nitro-, methyl-, ethyl-, n-propyl-, i-propyl-, methoxy-, ethoxy-, trifluoromethyl- or trifluoromethoxy-substituted phenyl or benzyl.

$R^3$ very particularly preferably represents optionally fluorine- or chlorine-substituted methyl, ethyl, n-propyl, iso-propyl, n-butyl, tert-butyl or in each case optionally fluorine-, chlorine-, bromine-, methyl-, ethyl-, iso-propyl-, tert-butyl-, methoxy-, ethoxy-, iso-propoxy-, trifluoromethyl-, trifluoromethoxy-, cyano- or nitro-substituted phenyl or benzyl.

$R^4$ and $R^5$ independently of one another each very particularly preferably represent in each case optionally fluorine- or chlorine-substituted $C_1$–$C_4$-alkyl, $C_1$–$C_4$-alkoxy, $C_1$–$C_4$-alkylamino, di-($C_1$–$C_4$-alkyl)amino or $C_1$–$C_4$-alkylthio or represent in each case optionally fluorine-, chlorine-, bromine-, nitro-, cyano-, methyl-, methoxy-, trifluoromethyl- or trifluoromethoxy-substituted phenyl, phenoxy or phenylthio.

$R^6$ and $R^7$ independently of one another each very particularly preferably represent hydrogen, represent in each case optionally fluorine- or chlorine-substituted $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_2$–$C_4$-alkyl, represent in each case optionally fluorine-, chlorine-, bromine-, methyl-, methoxy- or trifluoromethyl-substituted phenyl or benzyl or together represent an optionally methyl- or ethyl-substituted $C_5$–$C_6$-alkylene radical in which optionally one methylene group is replaced by oxygen or sulphur.

The abovementioned general or preferred radical definitions or illustrations can be combined with one another as desired, i.e. including combinations between the ranges and preferred ranges in question. They apply both to the end product and, correspondingly, to the precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings given above as being particularly preferred.

Very particular preference according to the invention is given to the compounds of the formula (I) which contain a combination of the meanings listed above as being very particularly preferred.

A preferred group of compounds of the formula (I) are those compounds in which $D^1$ and $D^2$ represent hydrogen.

Saturated or unsaturated hydrocarbon radicals, such as alkyl or alkenyl, can in each case be straight-chain or branched as far as is possible, including in combination with heteroatoms, such as, for example, in alkoxy.

Optionally substituted radicals may be mono- or polysubstituted, and, in the case of polysubstitions, the substituents may be identical or different.

In addition to the compounds mentioned in the Preparation Examples, the following compounds of the formula (I-1-a) may be mentioned specifically:

TABLE 1

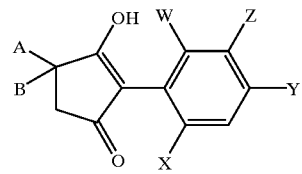

W = $CH_3$; X = $CH_3$; Y = $CH_3$; Z = $CH_3$

| A | B |
|---|---|
| $CH_3$ | $CH_3$ |
| $C_2H_5$ | $CH_3$ |
| $C_3H_7$ | $CH_3$ |
| i-$C_3H_7$ | $CH_3$ |
| $C_4H_9$ | $CH_3$ |
| i-$C_4H_9$ | $CH_3$ |
| s-$C_4H_9$ | $CH_3$ |
| t-$C_4H_9$ | $CH_3$ |
| $C_2H_5$ | $C_2H_5$ |
| $C_3H_7$ | $C_3H_7$ |
|  | $CH_3$ |
| 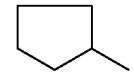 | $CH_3$ |
|  | $CH_3$ |
| —$(CH_2)_2$— | |
| —$(CH_2)_4$— | |
| —$(CH_2)_5$— | |
| —$(CH_2)_6$— | |
| —$(CH_2)_7$— | |
| —$CH_2$—O—$(CH_2)_3$— | |
| —$(CH_2)_2$—S—$(CH_2)_2$— | |
| —$CH_2$—O—$(CH_2)_3$— | |
| —$CH_2$—$CHCH_3$—$(CH_2)_3$— | |
| —$(CH_2)_2$—$CHCH_3$—$(CH_2)_2$— | |
| —$(CH_2)_2$—$CHC_2H_5$—$(CH_2)_2$— | |
| —$(CH_2)_2$—$CHC_3H_7$—$(CH_2)_2$— | |
| —$(CH_2)_2$—$CHi$-$C_3H_7$—$(CH_2)_2$— | |
| —$(CH_2)_2$—$CHOCH_3$—$(CH_2)_2$— | |
| —$(CH_2)_2$—$CHOC_2H_5$—$(CH_2)_2$— | |
| —$(CH_2)_2$—$CHOC_3H_7$—$(CH_2)_2$— | |
| —$(CH_2)_2$—$CHOi$-$C_3H_7$—$(CH_2)_2$— | |
| —$(CH_2)_2$—$C(CH_3)_2$—$(CH_2)_2$— | |
| —$CH_2$—$(CHCH_3)_2$—$(CH_2)_2$— | |

TABLE 1-continued

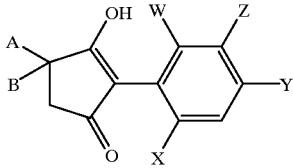

$W = CH_3; X = CH_3; Y = CH_3; Z = CH_3$

| A | B |
|---|---|
| —CH$_2$—CH—(CH$_2$)$_2$—CH—<br>└—CH$_2$—┘ | |
| —CH$_2$—CH————CH—CH$_2$—<br>└—(CH$_2$)$_4$—┘ | |
| —CH$_2$—CH————CH—(CH$_2$)$_2$—<br>└—(CH$_2$)$_3$—┘ | |

Table 2
  A and B are as defined in Table 1, and
  W=CH$_3$; X=CH$_3$; Y=H; Z=Cl
Table 3
  A and B are as defined in Table 1 and
  W=CH$_3$; X=CH$_3$; Y=CH$_3$; Z=F
Table
  A and B are as defined in Table 1 and
  W=CH$_3$; X=CH$_3$; Y=CH$_3$; Z=Cl
Table 5
  A and B are as defined in Table 1 and
  W=CH$_3$; X=CH$_3$; Y=CH$_3$; Z=Br
Table 6
  A and B are as defined in Table 1 and
  W=CH$_3$; X=CH$_3$; Y=H; Z=Br
Table 7
  A and B are as defined in Table 1 and
  W=Cl; X=Cl; Y=H; Z=Br
Table 8
  A and B are as defined in Table 1 and
  W=Br, X=Br; Y, Z=—(CH$_2$)$_3$—
Table 9
  A and B are as defined in Table 1 and
  W=CH$_3$; X=OCH$_3$; Y=H; Z=Br
Table 10
  A and B are as defined in Table 1 and
  W=CH$_3$; X=CH$_3$; Y=CH$_3$; Z=CH$_3$
Table 11
  A and B are as defined in Table 1 and
  W=Cl; X=Cl; Y=Cl; Z=CH$_3$
Table 12
  A and B are as defined in Table 1 and
  W=Br; X=Br; Y=Br; Z=CH$_3$
Table 13
  A and B are as defined in Table 1 and
  W=H; X=Cl; Y=Cl; Z=Cl
Table 14
  A and B are as defined in Table 1 and
  W=H; X=CH$_3$; Y=CH$_3$, Z=CH$_3$
Table 15
  A and B are as defined in Table 1 and
  W=H, X=CH$_3$; Y=Cl, Z=CH$_3$
Table 16
  A and B are as defined in Table 1 and
  W=H; X=Br, Y=CH$_3$; Z=Cl
Table 17
  A and B are as defined in Table 1 and
  W=H; X=Br; Y=CH$_3$; Z=CH$_3$
Table 18
  A and B are as defined in Table 1 and
  W=H; X=Cl; Y=Br, Z=CH$_3$
Table 19
  A and B are as defined in Table 1 and
  W=H; X=Cl; Y=Cl; Z=CH$_3$
Table 20
  A and B are as defined in Table 1 and
  W=H; X=CH$_3$; Y=CH$_3$; Z=Br
Table 21
  A and B are as defined in Table 1 and
  W=H; X=Cl; Y, Z=—CF$_2$—O—
Table 22
  A and B are as defined in Table 1 and
  W=H; X=Br; Y=CH$_3$; Z=Br
Table 23
  A and B are as defined in Table 1 and
  W=H; X=CH$_3$; Y=H; Z=CH$_3$
Table 24
  A and B are as defined in Table 1 and
  W=H; X=Cl; Y=H; Z=NO$_2$
Table 25
  A and B are as defined in Table 1 and
  W=H; X=Br; Y=H; Z=OCH$_3$ Using according to Process (A) ethyl 5-(2,4,6-trichloro-3-methylphenyl)-2,2-dimethyl-4-oxo-valerate as starting material, the course of the process according to the invention can be represented by the following reaction scheme:

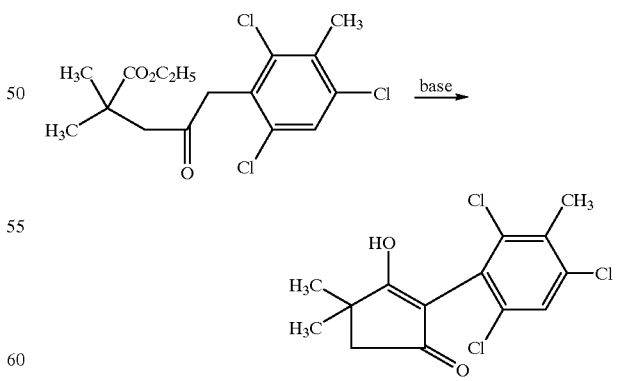

Using according to process (B) (variant α) 2-(2,4,6-trimethyl-3-chlorophenyl)-3-hydroxy-4,4-dimethyl-Δ$^2$-cyclopentenone and pivaloyl chloride as starting materials, the course of the process according to the invention can be represented by the following reaction scheme:

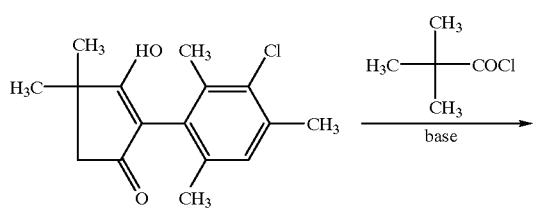

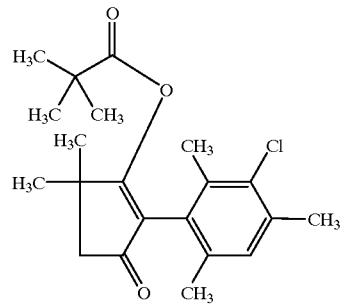

Using according to process (B) (variant β) 2-(2,5-dimethylphenyl)-3-hydroxy-4-methyl-4-phenyl-Δ²-cyclopentenone and acetic anhydride as starting materials, the course of the process according to the invention can be represented by the following reaction scheme:

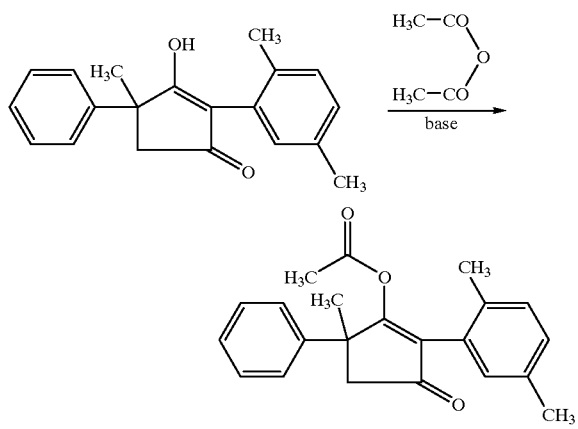

Using according to process (C) 2-(2,4-dichlor-5-methylphenyl)-3-hydroxy-4-isopropyl-4-methyl-Δ²-cyclopentenone and ethoxyethyl chloroformate as starting materials, the course of the process according to the invention can be represented by the following reaction scheme:

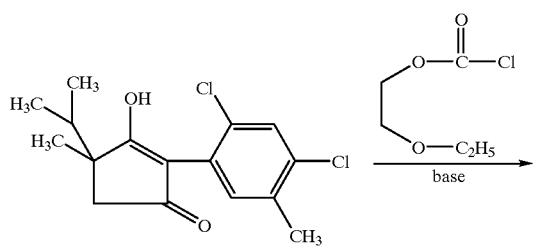

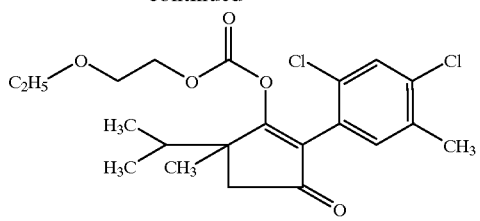

Using according to process (D) 2-(2,4,5-trimethylphenyl)-3-hydroxy-4-ethyl-4-methyl-Δ²-cyclopentenone and methyl chloromonothioformate as starting materials, the course of the reaction can be represented as follows:

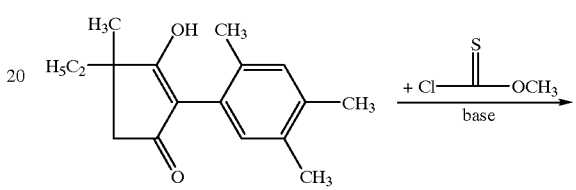

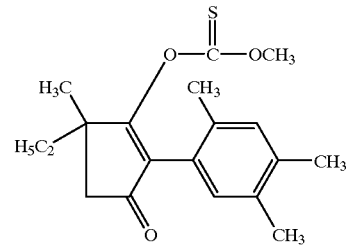

Using according to process (E) 2-(2,4,6trimethyl-3-bromophenyl)-3-hydroxy-4,4-(4-methoxy)-pentamethylene-Δ²-cyclopentenone and methanesulphonyl chloride as starting materials, the course of the reaction can be represented by the following reaction scheme:

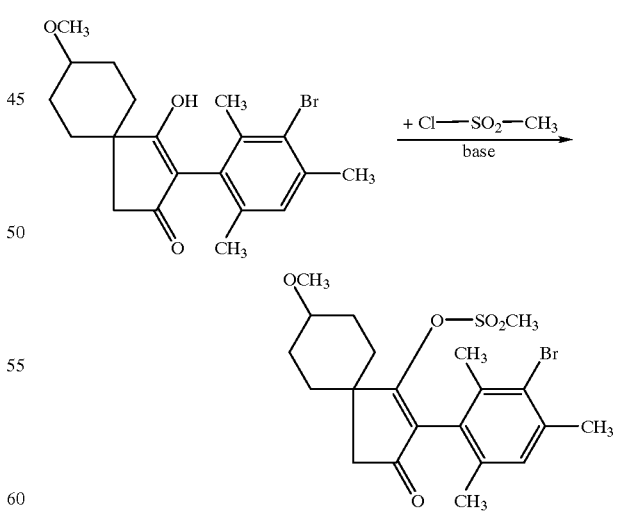

Using according to process (F) 2-(2,4,5-trimethylphenyl)-3-hydroxy-4,4-dimethyl-Δ²-cyclopentenone and 2,2,2-trifluoroethyl methanethio-phosphonyl chloride as starting materials, the course of the reaction can be represented by the following reaction scheme:

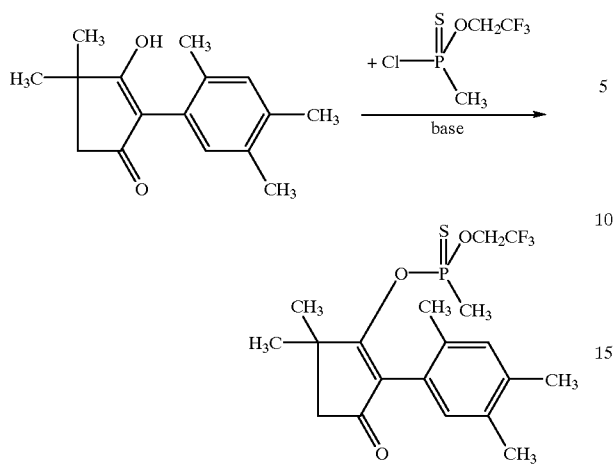

Using according to process (Gα) 2-(2,6-dimethyl-3-bromophenyl)-3-hydroxy-4,4-tetramethylene-Δ²-cyclopentenone and ethyl isocyanate as starting materials, the course of the reaction can be represented by the following reaction scheme:

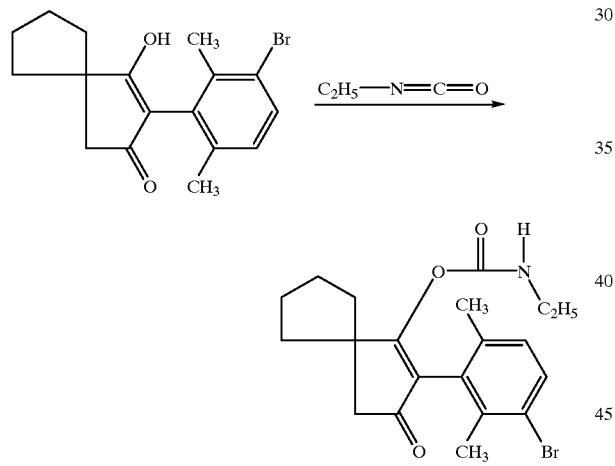

Using according to process (Gβ) 2-(2,3,4,6-tetramethylphenyl)-3-hydroxy-4-trifluoromethylmethyl-Δ²-cyclopentenone and dimethylcarbamoyl chloride as starting materials, the course of the reaction can be represented by the following scheme:

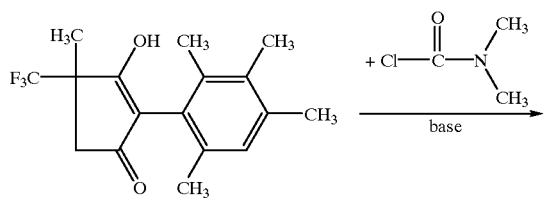

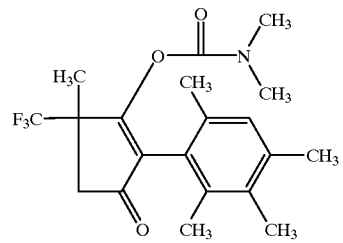

Using according to process (H) 2-(2,4,6-trimethyl-3-fluorophenyl)-3-hydroxy-4,4-dimethyl-Δ²-cyclopentenone and NAOH as components, the course of the process according to the invention can be represented by the following reaction scheme:

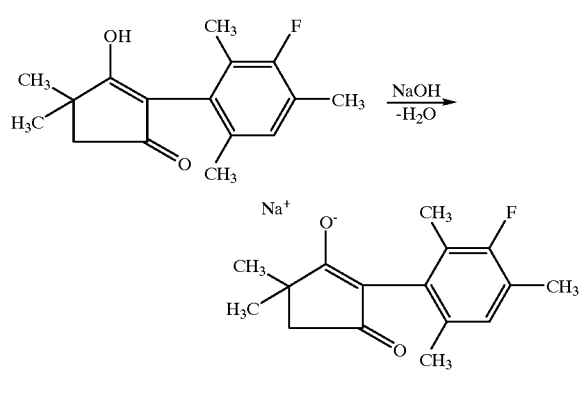

The compounds of the formula (II)

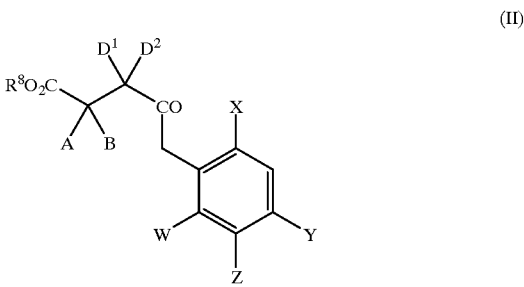

(II)

in which

A, B, $D^1$, $D^2$, W, X, Y, Z, n and $R^8$ are each as defined above, which are required as starting materials for the process (A) above are novel.

They can be prepared by methods known in principle.

The 5-aryl-4-ketocarboxylic esters of the formula (II) are obtained, for example, when 5-aryl-4-ketocarboxylic acids of the formula (XIII)

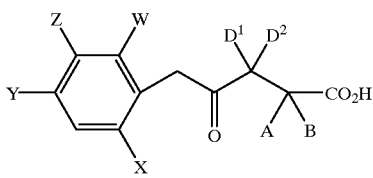
(XIII)

in which
W, X, Y, Z, A, B, $D^1$ and $D^2$ are each as defined above are esterified (cf., for example, Organikum, 15th Edition, Berlin, 1977, page 499) or alkylated (see Preparation Example).

The 5-aryl-4-ketocarboxylic acids of the formula (XIII)

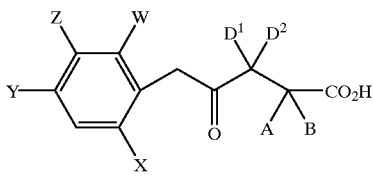
(XIII)

in which
A, B, $D^1$, $D^2$, W, X, Y and Z are each as defined above
are novel; however, they can be prepared by methods known in principle (see Preparation Example)

The 5-aryl-4-ketocarboxylic acids of the formula (XIII) are obtained, for example, when carboxylic anhydrides of the formula (XIV)

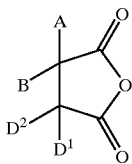
(XIV)

in which
A, B, $D^1$ and $D^2$ are each as defined above,
are reacted with organometallic compounds of the formula (XV)

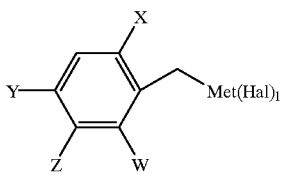
(XV)

in which
W, X, Y and Z are each as defined above,
Met represents mono- or divalent metal ions, for example those of lithium or magnesium,
Hal represents chlorine or bromine
and
l represents a number 0 or 1
in the presence of a diluent (cf., for example, Organikum, 15th Edition, Berlin, 1977, page 623).

Some of the compounds of the formulae (XIV) and (XV) are known, and/or they can be prepared by known processes (cf., for example, Organikum, 15th Edition, Berlin, 1977, pages 525, 526 and 623).

Furthermore, 5-aryl-4-ketocarboxylic acids of the formula (XIII)

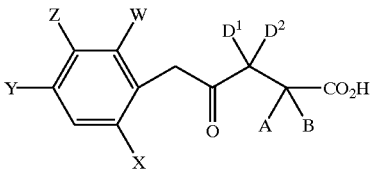
(XIII)

in which
A, B, $D^1$, $D^2$, W, X, Y and Z are each as defined above,
are obtained when 2-phenyl-3-oxo-adipates of the formula (XVI)

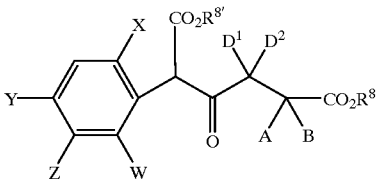
(XVI)

in which
A, B, $D^1$, $D^2$, W, X, Y and Z are each as defined above and $R^8$ and $R^{8'}$ represent alkyl (in particular $C_1$–$C_8$-alkyl)
are decarboxylated, if appropriate in the presence of a diluent and if appropriate in the presence of a base or an acid (cf., for example, Organikum, 15th Edition, Berlin, 1977, pages 519 to 521)

The compounds of the formula (XVI)

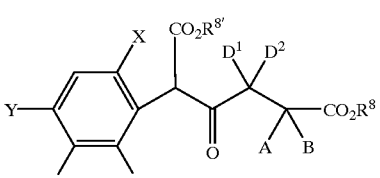
(XVI)

in which
A, B, $D^1$, $D^2$, W, X, Y, Z, $R^8$, $R^{8'}$ are each as defined above
are novel.

The compounds of the formula (XVI) are obtained, for example,
when dicarboxylic monoester chlorides of the formula (XVII)

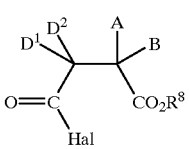
(XVII)

in which
A, B, D¹, D² and R⁸ are each as defined above and
Hal represents chlorine or bromine
or carboxylic anhydrides of the formula (XIV)

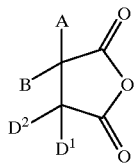

(XIV)

are acylated with a phenyl acetic ester of the formula (XVIII)

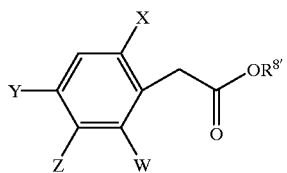

(XVIII)

in which
W, X, Y, Z and R⁸' are each as defined above
in the presence of a diluent and in the presence of a base (cf., for example, M. S. Chambers, E. J. Thomas, D. J. Williams, J. Chem. Soc. Chem. Commun., (1987), 1228, cf. also the Preparation Examples).

Some of the compounds of the formulae (XVII) are known compounds of organic chemistry, and/or they can be prepared in a simple manner by methods known in principle.

Some of the compounds of the formula (XVIII) are known (WO 97/36868, DE 196 31 586, WO 97/01535, DE 19 02 524) or they can be prepared by the process described therein.

The process (A) is characterized in that compounds of the formula (II) in which A, B, D¹, D², W, X, Y, Z and R⁸ are each as defined above are subjected to an intramolecular condensation in the presence of a base.

Suitable diluents for the process (A) according to the invention are all organic solvents which are inert towards the reaction participants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone. It is furthermore possible to employ alcohols, such as methanol, ethanol, propanol, iso-propanol, butanol, isobutanol, tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, calcium hydroxide, magnesium oxide, calcium oxide, sodium carbonate, potassium carbonate and calcium carbonate, which may also be employed in the presence of phase-transfer catalysts, such as, for example, triethylbenzylammonium chloride, tetrabutylammonium bromide, Adogen 464 (methyltrialkyl ($C_8$–$C_{10}$) ammonium chloride) or TDA 1 (tris-(methoxyethoxyethyl)-amine). Furthermore, it is possible to use alkali metals, such as sodium or potassium. Moreover, alkali metal and alkaline earth metal amides and hydrides, such as sodium amide, sodium hydride and calcium hydride, and moreover also alkali metal alkoxides, such as sodium methoxide, sodium ethoxide and potassium tert-butoxide, may be used.

When carrying out the process (A) according to the invention, the reaction temperatures can be varied within a relatively wide range. In general, the process is carried out at temperatures between −75° C. and 250° C., preferably between −50° C. and 150° C.

The process (A) according to the invention is generally carried out under atmospheric pressure.

When carrying out the process (A) according to the invention, the reaction components of the formula (II) and the deprotonating bases are generally employed in approximately equimolar amounts However, it is also possible to use a relatively large excess (up to 3 mol) of one or the other component.

The process (Bα) is characterized in that compounds of the formula (Ia) are reacted with carbonyl halides of the formula (III), if appropriate in the presence of a diluent and if appropriate in the presence of an acid binder.

Suitable diluents for the process (Bα) according to the invention are all solvents which are inert towards the acyl halides. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethylformamide, dimethyl sulphoxide and sulpholane. The stability of the acyl halide hydrolysis permitting, it is also possible to carry out the reaction in the presence of water.

Suitable acid binders for the reaction according to the process (Bα) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

When carrying out the process (Bα) according to the invention, the reaction temperature can be varied within a relatively wide range. In general, the process is carried out at temperatures between −20° C. and +150° C., preferably between 0° C. and 100° C.

When carrying out the process (Bα) according to the invention, the starting materials of the formula (Ia) and the carbonyl halide of the formula (III) are generally employed in approximately equivalent amounts. However, it is also possible to use a relatively large excess (for example up to 5 mol) of the carbonyl halide. Work-up is carried out by customary methods.

The process (Bβ) is characterized in that compounds of the formula (Ia) are reacted with carboxylic anhydrides of the formula (IV), if appropriate in the presence of a diluent and if appropriate in the presence of an acid binder.

Suitable diluents for the process (Bβ) according to the invention are preferably those diluents which are also preferred when acyl halides are used. Besides, it is also possible for a carboxylic anhydride employed in excess to act simultaneously as diluents.

In the process (Bβ), preferred acid binders, which are added if appropriate, are those acid binders which are also preferred when acyl halides are used.

When carrying out the process (Bβ) according to the invention, the reaction temperature can be varied within a relatively wide range. In general, the process is carried out at temperatures between −20° C. and +150° C., preferably between 0° C. and 100° C.

When carrying out the process (Bβ) according to the invention, the starting materials of the formula (I-a) and the carboxylic anhydride of the formula (IV) are generally employed in approximately equivalent amounts. However, it is also possible to employ a relatively large excess (up to 5 mol) of the carboxylic anhydride. Work-up is carried out by customary methods.

In general, a procedure is used in which diluent and excess carboxylic anhydride and the resulting carboxylic acid are removed by distillation or by washing with an organic solvent or with water.

The process (C) is characterized in that compounds of the formula (I-a) are reacted with chloroformic esters or chloroformic thioesters of the formula (V), if appropriate in the presence of a diluent and if appropriate in the presence of an acid binder.

Suitable acid binders for the process (C) according to the invention are all customary acid acceptors. Preference is given to using tertiary amines, such as triethylamine, pyridine, DABCO, DBU, DBA, Hünig base and N,N-dimethylaniline, furthermore alkaline earth metal oxides, such as magnesium oxide and calcium oxide, additionally alkali metal and alkaline earth metal carbonates, such as sodium carbonate, potassium carbonate and calcium carbonate, and also alkali metal hydroxides, such as sodium hydroxide and potassium hydroxide.

Suitable diluents for the process (C) according to the invention are all solvents which are inert towards the chloroformic esters or chloroformic thioesters. Preference is given to using hydrocarbons, such as benzine, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, moreover nitriles, such as acetonitrile, and also strongly polar solvents, such as dimethylformamide, dimethyl sulphoxide and sulpholane.

When carrying out the process (C) according to the invention, the reaction temperature can be varied within a relatively wide range. The reaction temperature is generally between −20° C. and +100° C., preferably between 0° C. and 50° C.

The process (C) according to the invention is generally carried out under atmospheric pressure.

When carrying out the process (C) according to the invention, the starting materials of the formula (I-a) and the appropriate chloroformic ester or chloroformic thioester of the formula (V) are generally in each case employed in approximately equivalent amounts. However, it is also possible to employ a relatively large excess (for example up to 2 mol) of one or the other components. Work-up is carried out by customary methods. In general, a procedure is used in which precipitated salts are removed and the reaction mixture which remains is concentrated by stripping off the diluent.

The process (D) according to the invention is characterized in that compounds of the formula (I-a) are reacted with compounds of the formula (VI) in the presence of a diluent and, if appropriate, in the presence of an acid binder.

In the preparation process (D), approximately 1 Mol of chloromonothioformic ester or chlorodithioformic ester of the formula (VI) is employed per mole of starting material of the formula (I-a), at from 0 to 120° C., preferably from 20 to 60° C.

Diluents which may be added, if appropriate, are all inert polar organic solvents, such as ethers, amides, sulphones, sulphoxides, and also halogenoalkanes.

Preference is given to using dimethyl sulphoxide, tetrahydrofuran, dimethylformamide or methylene chloride.

If, in a preferred embodiment, the enolate salt of the compounds (I-a) is prepared by addition of strong deprotonating agents, such as, for example, sodium hydride or potassium tert-butoxide, the further addition of acid binders can be dispensed with.

If acid binders are used, customary inorganic or organic bases are suitable. Sodium hydroxide, sodium carbonate, potassium carbonate, pyridine and triethylamine may be mentioned by way of example.

The reaction can be carried out under atmospheric pressure or under elevated pressure and is preferably carried out under atmospheric pressure. Work-up is carried out by customary methods.

The process (E) according to the invention is characterized in that compounds of the formula (I-a) are reacted with sulphonyl chlorides of the formula (VII), if appropriate in the presence of a diluent and if appropriate in the presence of an acid binder. In the preparation process (E), approximately 1 mol of sulphonyl chloride of the formula (VII) is employed per mole of starting material of the formula (I-a), at from −20 to 150° C., preferably from 0 to 70° C.

The process (E) is preferably carried out in the presence of a diluent.

Suitable diluents are all inert polar organic solvents, such as ethers, amides, ketones, carboxylic esters, nitrites, sulphones, sulphoxides or halogenated hydrocarbons, such as methylene chloride.

Preference is given to using dimethyl sulphoxide, tetrahydrofuran, dimethylformamide, methylene chloride.

If, in a preferred embodiment, the enolate salt of the compound of the formula (I-a) is prepared by addition of strong deprotonating agents (such as, for example, sodium hydride or potassium tert-butoxide), the further addition of acid binders can be dispensed with.

If acid binders are used, customary inorganic or organic bases are suitable. Sodium hydroxide, sodium carbonate, potassium carbonate, pyridine and triethylamine may be mentioned by way of example.

The reaction can be carried out under atmospheric pressure or under elevated pressure and is preferably carried out under atmospheric pressure. Work-up is carried out by customary methods.

The process (F) according to the invention is characterized in that compounds of the formula (I-a) are reacted with phosphorus compounds of the formula (VIII), if appropriate in the presence of a diluent and if appropriate in the presence of an acid binder.

In the preparation process (F), in order to obtain compounds of the formula (I-e), from 1 to 2, preferably from 1 to 1.3, mol of the phosphorus compound of the formula (VIII) are reacted per mole of the compound (I-a), at temperatures between 40° C. and 150° C., preferably between −10 and 110° C.

The process (F) is preferably carried out in the presence of a diluent Suitable diluents are all inert, polar organic solvents, such as ethers, carboxylic esters, halogenated hydrocarbons, ketones, amides, nitriles, sulphones, sulphoxides, etc.

Preference is given to using acetonitrile, dimethyl sulphoxide, tetrahydrofuran, dimethylformamide, methylene chloride.

Acid binders which may be added, if appropriate, are customary inorganic or organic bases, such as hydroxides, carbonates or amines. Sodium hydroxide, sodium carbonate, potassium carbonate, pyridine and triethylamine may be mentioned by way of example.

The reaction can be carried out under atmospheric pressure or under elevated pressure and is preferably carried out under atmospheric pressure. Work-up is carried out by customary methods of organic chemistry. The end products are preferably purified by crystallization, chromatographic purification or by so-called "incipient distillation", i.e. removal of the volatile components under reduced pressure.

The process (G) according to the invention is characterized in that compounds of the formula (I-a) are (Gα) reacted with compounds of the formula (XI), if appropriate in the presence of a diluent and if appropriate in the presence of a catalyst, or (Gβ) reacted with compounds of the formula (XII), if appropriate in the presence of a diluent and if appropriate in the presence of an acid binder.

In the preparation process (Gα), approximately 1 mol of isocyanate of the formula (XI) is reacted per mole of starting material of the formula (I-a), at from 0 to 100° C., preferably at from 20 to 50° C.

The process (Gα) is preferably carried out in the presence of a diluent.

Suitable diluents are all inert organic solvents, such as aromatic hydrocarbons, halogenated hydrocarbons, ethers, amides, nitrites, sulphones or sulphoxides.

If appropriate, catalysts may be added to accelerate the reaction. Catalysts which can be employed very advantageously are organotin compounds, such as, for example, dibutyltin dilaurate.

The process is preferably carried out under atmospheric pressure.

In the preparation process (Gβ), approximately 1 mol of carbamoyl chloride of the formula (XII) is reacted per mole of starting material of the formula (I-a), at from 0 to 150° C., preferably at from 20 to 70° C.

Diluents which may be added, if appropriate, are all inert polar organic solvents, such as ethers, carboxylic esters, nitriles, ketones, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compound (I-a) is prepared by addition of strong deprotonating agents (such as, for example, sodium hydride or potassium tert-butoxide), the further addition of acid binders may be dispensed with.

If acid binders are used, customary inorganic or organic bases are suitable. Sodium hydroxide, sodium carbonate, potassium carbonate, triethylamine or pyridine may be mentioned by way of example.

The reaction can be carried out under atmospheric pressure or under elevated pressure and is preferably carried out under atmospheric pressure. Work-up is carried out by customary methods.

The process (H) is characterized in that compounds of the formula (I-f) are in each case reacted with metal hydroxides or metal alkoxides of the formula (IX) or amines of the formula (X), if appropriate in the presence of a diluent.

Preferred diluents for the process (H) according to the invention are ethers, such as tetrahydrofuran, dioxane, diethyl ether, or else alcohols, such as methanol, ethanol, isopropanol, and also water. The process (H) according to the invention is generally carried out under atmospheric pressure. The reaction temperature is generally between −20° C. and 100° C., preferably between 0° C. and 50° C.

The active compounds are suitable for controlling animal pests, preferably anthropodes and nematodes, in particular insects and arachnids, encountered in agriculture, in forests, in the protection of stored products and of materials, and in the hygiene sector. They are active against normally sensitive and resistant species, and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blatella gennanica, Acheta domesticus,* Gryllotalpa spp., *Locusta migratoria migratorioides, Melanoplus differentialis* and *Schistocerca gregana.*

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., *Pediculus humanus corporis,* Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphurn padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thuiberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuelmiella, Galleria mellonella, Tineola bisselliella, Tinea pellionella, Hofinannophila pseudospretella, Cacoecia*

*podana, Capua reticulana, Choristoneura flrnferana, Clysia ambiguella, Homona magnanima* and *Tortrix viridana.*

From the order of the Coleoptera, for example, *Anobium punctatum, Rhizopertha dorninica, Ancanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varive stis,* Atomaria spp., *Oxyzaephilus surinamensis,* Antho nomus spp., Sitophilus spp., *Otiorrhynchus sulcatus, Cosmopolites sordidus, Ceuthorrhynchus assimilis, Hypera posfica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Cono derus spp., *Melolontha melolontha, Amphimallon solsti tialis* and *Costelytra zealandica.*

From the order of the Hymenoptera, for example, Diprion spp., Hoplocampa spp., Lasius spp., *Monomorium pbaraonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp, Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

In particular, the active compounds according to the invention have excellent insecticidal and acaricidal activity.

They can be used particularly successfully for controlling plant-damaging insects, for example against the larvae of the mustard beetle (*Phaedon cochleariae*) or against the larvae of the green rice leaf hopper (*Nephotettix cincticeps*) or against caterpillars of the diamond back moth (*Plutella maculipennis*).

The active compounds according to the invention can furthermore be used as defoliants, desiccants, haulm-killers and, especially, as weedkillers. By weeds, in the broadest sense, are to be understood all plants which grow in locations where they are unwanted. Whether the substances according to the invention act as total or selective herbicides depends essentially on the amount used.

The dosages of the active compounds according to the invention required for controlling weeds are between 0.001 and 10 kg/ha, preferably between 0.005 and 5 kg/ha.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cycnodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Sachharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pastureland, and for the selective control of weeds in annual crops.

The active compounds according to the invention are highly suitable for the selective control of monocotyledonous weeds in dicotyledonous crops by both the pre- and the post-emergence method. They can be employed very successfully for controlling harmful grasses for example in cotton or sugar beet.

The active compounds can be converted into the customary formulations, such as solutions, emulsions, wettable powders, suspensions, powders, dusting agents, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use for example organic solvents as auxiliary solvents. Essentially, suitable liquid solvents are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol and their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, suitable solid carriers for granules are: for example crushed and fractionated natural rocks such as calcite, marble, pumice, sepiolite and dolomite and synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulphonates, alkylsulphates, arylsulphonates and protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, and natural phospholipids such as cephalins and lecithins, and synthetic phospholipids, can be used in the formulations. Possible further additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compound according to the invention can be present in its commercially available formulations and in the use forms prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms.

Examples of particularly advantageous mixture components are the following compounds:
Fungicides:
2-aminobutane; 2-anilino4-methyl-6cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6(2-cyanophenoxy)-pyrimidin-4-yloxy]-phenyl}-3-methoxyacrylate; methyl (E)-methoximino-[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazirn, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferirnzone, fluazinam, fludioxonil, fluoromide, fluquinconazole, flusilazole, flusulphamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulphocarb, methfuroxam, metiram, metsulphovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebucanozole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumnizole, triforine, triticonazole, validamycin A, vinclozolin, zineb, ziram.
Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, AC 303 630, acephate, acrinathrin, alanycarb, aldicarb, alphamethrin, amitraz, avermectin, AZ 60541, azadirachtin, azinphos A, azinphos M, azocyclotin. Bacillus thuringiensis, bendiocarb, benfuracarb, bensultap, beta-cyfluthrin, bifenthrin, BPMC, brofenprox, bromophos A, bufencarb, buprofezin, butocarboxin, butylpyridaben, cadusafos, carbaryl, carbofuran, carbophenothion, carbosulphan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulphoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivermectin, lambda-cyhalothrin, lufenuron, malathion, mecarbam, mevinphos, mesulphenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyradaphenthion, pyresmetirin, pyretirum, pyridaben, pyrimidifen, pyriproxifen, quinalphos,

RH 5992, salithion, sebufos, silafluofen, sulphotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamnidothion, XMC, xylylcarb, YI 5301/5302, zetamethrin.

Herbicides:

for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr, aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimeihalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenz-thiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulphuron, bensulphuron-methyl, chlorimuron-ethyl, chlorsulphuron, cinosulphuron, metsulphuron-methyl, nicosulphuron, primisulphuron, pyrazosulphuron-ethyl, thifensulphuron-methyl, triasulphuron and tribenuron-methyl; thiolcarbamates such as, for example, butylate, cycloate, di-allate, EPTC, esprocarb, molinate, prosulphocarb, thiobencarb and tri-allate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane The active compound according to the invention can furthermore be present in its commercially available formulations and in the use forms prepared from these formulations, as a mixture with synergistic agents Synergistic agents are compounds which increase the action of the active compounds without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound has an excellent residual action on wood and clay and a good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp., Solenopotes spp..

From the order of the Mallophagida and the suborders Amblycerina and Ischnocerina, for example, Trimenopon spp., Menopon spp., Trinoton spp., Bovicola spp., Wemeckiella spp., Lepikentron spp., Damalina spp., Trichodectes spp., Felicola spp..

From the order Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp., From the order of the Siphonapterida, for example, Pulex spp., Ctenocephalides spp., Xenopsylla spp. and Ceratophyllus spp..

From the order of the Heteropterida, for example, Cimex spp., Triatoma spp., Rhodnius spp. and Panstrongylus spp..

From the order of the Blattarida, for example, *Blatta orientalis, Periplaneta americana, Blattela germanica* and Supella spp..

From the sub-class of the Acaria (Acarida) and the orders of the Meta- and Mesostigmata, for example Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Sternostoma spp. and Varroa spp..

From the order of the Actinedida (Prostigmata) and Acaridida (Astigmata), for example Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Octodectes spp., Sarcoptes spp., Notoedres spp., Knemidocoptes spp., Cytodites spp. and Laminosioptes spp..

For example, they show an outstanding activity against *Boophilus microplus.*

The active compounds of the formula (I) according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, cage birds, aquarium fish, and so-called experimental animals such as, for example, hamsters, guinea-pigs, rats and mice. By controlling these arthropods, it is intended to reduce mortality and decreased performance (in meat, milk, wool, hides, eggs, honey and the like), so that more economical and simpler animal husbandry is made possible by using the active compounds according to the invention.

In the veterinary sector, the active compounds according to the invention are used in a known manner by enteral administration, for example in the form of tablets, capsules, drinks, drenches, granules, pastes, boluses, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10,000, or they may be used in the form of a chemical bath.

Furthermore, it has been found that the compounds of the formula (I) according to the invention have a potent insecticidal action against insects which destroy industrial materials.

The following insects may be mentioned by way of example and as being preferred, but without any limitation:

Beetles, such as

*Hylotrupes bajulus, Chlorophorus pilosis, Anobium punctatum, Xestobium rufovillosum, Ptilinus pecticornis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis,* Xyleborus spec. Tryptodendron spec. *Apate monachus, Bostrychus capucins, Heterobostrychus brunneus,* Sinoxylon spec., *Dinoderus minutus.*

Dermapterans, such as

*Sirex juvencus, Urocerus gigas, Urocerus gigas taignus, Urocerus augur.*

Termites, such as

Kalotermes flavicollis, Cryptotermes brevis, Heterotemnes indicola, Reticulitermes flavipes, Reticulitermes santonensis, Reticulitermes lucifugus, Mastotermes darwiniensis, Zootermopsis nevadensis, Coptotermes formosanus.

Bristletails, such as

Lepisma saccharina.

Industrial materials are to be understood as meaning, in the present context, non-live materials such as, preferably, plastics, glues, sizes, paper and board, leather, wood and timber products, and paint.

The materials to be very particularly protected against attack by insects are wood and timber products.

Wood and timber products which can be protected by the composition according to the invention or mixtures comprising such a composition are to be understood as meaning, for example: construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flash point of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range of 160 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spinde oil and/or monochloronaphthalene, preferably x-monochloronaphthalene, are used.

The organic oily or oil-type solvents of low volatility having an evaporation number of above 35 and a flash point of above 30° C., preferably above 45° C., can be partially replaced by organochemical solvents of high or medium volatility, with the proviso that the solvent mixture also has an evaporation number of above 35 and a flash point of above 30° C., preferably above 45° C., and that the insecticide/fungicide mixture is soluble or emulsifiable in this solvent mixture.

According to a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ethers, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colorants, pigments, water repellents, odour-masking substances and inhibitors or anti-corrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluene-sulphonic esters.

Fixatives are chemically based on polyvinyl alkyl ethers, such as, for example, polyvinyl methyl ether, or ketones, such as benzophenone or ethylene benzophenone.

Also particularly suitable as a solvent or diluent is water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94129 268. The compounds mentioned in that document are expressly part of the present application.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole, metconazole, imazalil, dichlorofluanide, tolylfluanide, 3-iodo-2-propinyl-butyl carbamate, N octyl-isothiazolin-3-one and 4,5-dichloro-N-octylisothiazolin-3-one.

The preparation and the use of the active compounds according to the invention can be seen from the examples below.

PREPARATION EXAMPLES

Example Ia-1

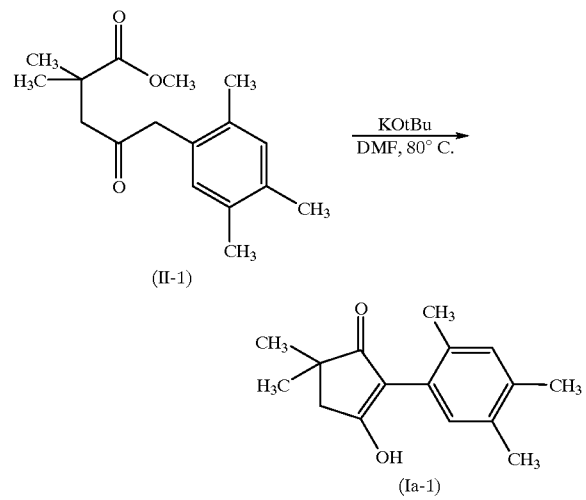

2.7 g (24 mmol) of potassium tert-butoxide are added to a solution of the compound according to Example II-1 (4.4 g, 16 mmol) in DMF (30 ml), and the mixture is stirred at 80° C. for 1 hour. With cooling using an ice bath, the mixture is stirred into approximately 600 ml of 1 NHCl, and the solid is filtered off with suction and dried Crude yield: 4 g (Δ100% of theory). M.p. 185–186° C.

Analogously, and/or in accordance with the general preparation procedures, the compounds of the formula (Ia) listed in Table 27, which are shown in the form of one of the possible isomers, were prepared.

TABLE 27

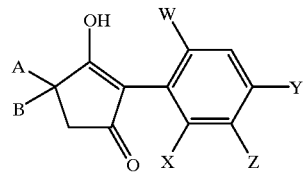

(Ia)

Table 28, Examples Ia

| Ex. No. | A | B | W | X | Y | Z | m.p. ° C. |
|---|---|---|---|---|---|---|---|
| Ia-2 | —(CH$_2$)$_5$— | | H | CH$_3$ | H | CH$_3$ | 202 |
| Ia-3 | —(CH$_2$)$_5$— | | H | CH$_3$ | CH$_3$ | CH$_3$ | 218 |
| Ia-4 | —(CH$_2$)$_5$— | | CH$_3$ | CH$_3$ | CH$_3$ | CH$_3$ | >250 |
| Ia-5 | —(CH$_2$)$_2$—CHCH$_3$—(CH$_2$)$_2$— | | H | CH$_3$ | CH$_3$ | CH$_3$ | 212 |
| Ia-6 | —(CH$_2$)$_4$— | | H | CH$_3$ | H | CH$_3$ | 174–175 |
| Ia-7 | —(CH$_2$)$_4$— | | H | CH$_3$ | CH$_3$ | CH$_3$ | 162–164 |
| Ia-8 | —(CH$_2$)$_5$— | | H | CH$_3$ | Cl | CH$_3$ | 202–203 |
| Ia-9 | —(CH$_2$)$_5$— | | CH$_3$ | H | H | CF$_3$ | 217–218 |
| Ia-10 | —(CH$_2$)$_2$—CHCH$_3$—(CH$_2$)$_2$— | | H | Br | CH$_3$ | CH$_3$ | 178–181 |
| Ia-11 | —(CH$_2$)$_2$—CHCH$_3$—(CH$_2$)$_2$— | | H | CH$_3$ | H | CH$_3$ | 196–198 |
| Ia-12 | —(CH$_2$)$_2$—CHCH$_3$—(CH$_2$)$_2$— | | CH$_3$ | CH$_3$ | CH$_3$ | F | 195–197 |
| Ia-13 | —(CH$_2$)$_3$—CHCH$_3$—CH$_2$— | | H | CH$_3$ | H | CH$_3$ | 71–73 |
| Ia-14 | —(CH$_2$)$_2$—CHOCH$_3$—(CH$_2$)$_2$— | | H | CH$_3$ | H | CH$_3$ | 215–217 |
| Ia-15 | —(CH$_2$)$_2$—CHOCH$_3$—(CH$_2$)$_2$— | | H | CH$_3$ | Cl | CH$_3$ | 179–180 |
| Ia-16 | —(CH$_2$)$_2$—CHOCH$_3$—(CH$_2$)$_2$— | | H | CH$_3$ | CH$_3$ | CH$_3$ | 186–188 |
| Ia-17 | —(CH$_2$)$_2$—CHOCH$_3$—(CH$_2$)$_2$— | | CH$_3$ | CH$_3$ | CH$_3$ | CH$_3$ | 233–235 |
| Ia-18 | —(CH$_2$)$_2$—O—(CH$_2$)$_2$— | | H | Br | CH$_3$ | CH$_3$ | 196–198 |
| Ia-19 | —(CH$_2$)$_2$—O—(CH$_2$)$_2$— | | H | Cl | H | CH$_2$CH$_3$ | 146–154 |
| Ia-20 | —(CH$_2$)$_2$—O—(CH$_2$)$_2$— | | H | CH$_3$ | H | CH$_3$ | >215 |
| Ia-21 | —(CH$_2$)$_2$—O—(CH$_2$)$_2$— | | CH$_3$ | CH$_3$ | CH$_3$ | CH$_3$ | >250 |

Example Ib-1

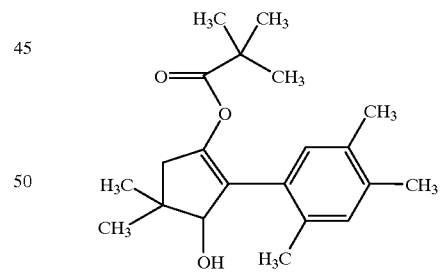

1.5 g (6.0 mmol) of the compound of Example Ia-1 are initially charged in 20 ml of dry methylene chloride and admixed with 1.25 ml (9.0 mmol; 1.5 eq) of triethylamine.

A solution of 1.16 ml (1.14 g, 9.0 mmol; 1.5 eq) of pivaloyl chloride in 3 ml of dry methylene chloride is added dropwise with ice-cooling. The mixture is stirred at room temperature for 1 to 2 hours and washed twice with 10% strength citric acid, and the combined aqueous acidic phases are extracted with methylene chloride. The combined organic phases are washed twice with 1 N NaOH and the aqueous alkaline phases are extracted with methylene chloride. The combined organic phases are combined and concentrated.

Yield: 1.90 g (96.00% of theory). M.p. 75–77° C.

Analogously, and/or in accordance with the general preparation procedures, the compounds of the formula (Ib) listed in Table 28, which are shown in the form of one of the possible isomers, were prepared.

TABLE 28

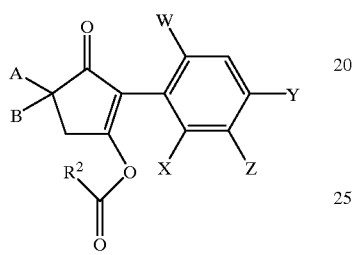

(Ib)

Table 28, Examples Ib

| Ex. No. | W | X | Y | Z | A | B | R¹ | m.p. ° C. |
|---|---|---|---|---|---|---|---|---|
| Ib-2 | H | $CH_3$ | H | $CH_3$ | —$(CH_2)_5$— | | $s$-$C_4H_9$ | 105 |
| Ib-3 | H | $CH_3$ | H | $CH_3$ | —$(CH_2)_5$— | | $t$-$C_4H_9$—$CH_2$ | 110 |
| Ib-4 | H | $CH_3$ | $CH_3$ | $CH_3$ | —$(CH_2)_5$— | | $t$-$C_4H_9$ | 108 |
| Ib-5 | H | $CH_3$ | $CH_3$ | $CH_3$ | —$(CH_2)_5$— | | $i$-$C_3H_7$ | 62 |
| Ib-6 | H | $CH_3$ | $CH_3$ | $CH_3$ | —$(CH_2)_2$—$CHCH_3$—$(CH_2)_2$— | | $t$-$C_4H_9$ | 92 |
| Ib-7 | H | $CH_3$ | $CH_3$ | $CH_3$ | —$(CH_2)_2$—$CHCH_3$—$(CH_2)_2$— | | $C_2H_5$—O—$CH_2$— | 185 |
| Ib-8 | $CH_3$ | $CH_3$ | $CH_3$ | $CH_3$ | —$(CH_2)_5$— | | $t$-$C_4H_9$ | 131–132 |
| Ib-9 | $CH_3$ | $CH_3$ | $CH_3$ | $CH_3$ | —$(CH_2)_5$— | | $C_2H_5$—O—$CH_2$— | wax |
| Ib-10 | H | $CH_3$ | $CH_3$ | $CH_3$ | —$(CH_2)_4$— | | $t$-$C_4H_9$ | 80–83 |
| Ib-11 | H | $CH_3$ | $CH_3$ | $CH_3$ | —$(CH_2)_4$— | | $C_2H_5$—O—$CH_2$— | 137–141 |
| Ib-12 | H | $CH_3$ | Cl | $CH_3$ | —$(CH_2)_5$— | | $t$-$C_4H_9$ | 123–126 |
| Ib-13 | $CH_3$ | H | H | $CF_3$ | —$(CH_2)_5$— | | $t$-$C_4H_9$ | 86–88 |
| Ib-14 | $CH_3$ | H | H | $CF_3$ | —$(CH_2)_5$— | | $C_2H_5$—O—$CH_2$— | wax |
| Ib-15 | H | Br | $CH_3$ | $CH_3$ | —$(CH_2)_2$—$CHCH_3$—$(CH_2)_2$— | | $s$-$C_4H_9$ | oil |
| Ib-16 | H | $CH_3$ | H | $CH_3$ | —$(CH_2)_2$—$CHCH_3$—$(CH_2)_2$— | | $t$-$C_4H_9$ | oil |
| Ib-17 | H | $CH_3$ | H | $CH_3$ | —$(CH_2)_2$—$CHCH_3$—$(CH_2)_2$— | | Cl—$CH_2$—$C(CH_3)_2$— | wax |
| Ib-18 | $CH_3$ | $CH_3$ | $CH_3$ | F | —$(CH_2)_2$—$CHCH_3$—$(CH_2)_2$— | | $t$-$C_4H_9$ | oil |
| Ib-19 | H | $CH_3$ | H | $CH_3$ | —$(CH_2)_3$—$CHCH_3$—$CH_2$— | | $t$-$C_4H_9$ | oil |
| Ib-20 | H | $CH_3$ | H | $CH_3$ | —$(CH_2)_2$—$CHOCH_3$—$(CH_2)_2$— | | $t$-$C_4H_9$ | oil |
| Ib-21 | H | $CH_3$ | Cl | $CH_3$ | —$(CH_2)_2$—$CHOCH_3$—$(CH_2)_2$— | | $t$-$C_4H_9$ | 116–118 |
| Ib-22 | H | $CH_3$ | $CH_3$ | $CH_3$ | —$(CH_2)_2$—$CHOCH_3$—$(CH_2)_2$— | | $t$-$C_4H_9$ | wax |
| Ib-23 | $CH_3$ | $CH_3$ | $CH_3$ | $CH_3$ | —$(CH_2)_2$—$CHOCH_3$—$(CH_2)_2$— | | $t$-$C_4H_9$ | 125–130 |
| Ib-24 | H | Br | $CH_3$ | $CH_3$ | —$(CH_2)_2$—O—$(CH_2)_2$— | | $s$-$C_4H_9$ | wax |
| Ib-25 | H | Cl | H | $CH_2CH_3$ | —$(CH_2)_2$—O—$(CH_2)_2$— | | $t$-$C_4H_9$ | oil |
| Ib-26 | H | $CH_3$ | H | $CH_3$ | —$(CH_2)_2$—O—$(CH_2)_2$— | | $t$-$C_4H_9$ | wax |
| Ib-27 | $CH_3$ | $CH_3$ | $CH_3$ | $CH_3$ | —$(CH_2)_2$—O—$(CH_2)_2$— | | $t$-$C_4H_9$ | 122–125 |
| Ib-28 | $CH_3$ | $CH_3$ | $CH_3$ | $CH_3$ | —$(CH_2)_2$—O—$(CH_2)_2$— | | $i$-$C_3H_7$ | 88–90 |

Example Ic-1

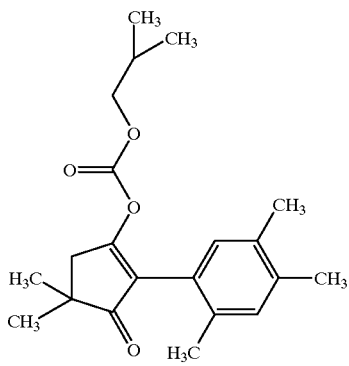

1.5 g (6.0 mmol) of the compound of Example Ia-I are initially charged in 20 ml of dry methylene chloride and admixed with 1.25 ml (9.0 mmol; 1.5 eq) of triethylamine.

A solution of 1.17 ml (1.23 g, 9.0 mmol; 1.5 eq) of isobutyl chloroformate in 3 ml of dry methylene chloride is added dropwise with ice-cooling. The mixture is stirred at room temperature for 1 to 2 hours.

Work-up is carried out as described under Example Ib- 1.

Yield: 2.00 g of oil. 97% of theory.

$^1$H NMR (400 MHz, CDCl$_3$): 0.9 (d, 6H, CH(CH$_3$)$_2$); 1.2 (s, 6H, CH(CH$_3$)$_2$); 1.9 (m, 1H, CH(CH$_3$)$_2$); 2.1 (s, 3H, ArCH$_3$); 2.2 (d, 6H, 2×ArCH$_3$), 2.9 (s, 2H, CH$_2$); 3.9 (d, 2H, OCH$_2$); 6.8; 7.0 (s, 2H, Ar—H).

Analogously, and/or in accordance with the general preparation procedures, the compounds of the formula (Ic) listed in Table 29, which are shown in the form of one of the possible isomers, were prepared.

Example If-1

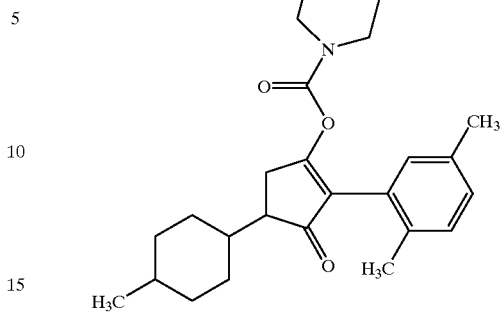

1.0 g (3.5 mmol) of the compound of Example Ia- I1 is initially charged in 30 ml of dried ethyl acetate and mixed with 0.73 ml (5.2 mmol; 1.5 eq) of triethylamine.

A solution of 0.53 ml (0.68 g; 4.6 mmol; 1.3 eq) of morpholine-N-carbonyl chloride in 5 ml of dry ethyl acetate is added dropwise at room temperature. The mixture is heated under reflux for 4 hours.

The mixture is concentrated using a rotary evaporator and taken up in methylene chloride. The mixture is washed twice with 0.5 N NaOH. The organic phase is dried and concentrated.

Yield: 1.0 g (72% of theory) of oil.

$^1$H NMR (400 MHz, DMSO-d$_6$): 0.95 (d, 31, CHCH$_3$); 1.3–1.8 (m, 9H, cyclohexyl-H); 2.05 (s, 3H, ArCH$_3$); 2.25 (s, 3H, ArCH$_3$); 2.9 (s, 2H, CH$_2$); 3.2–3.8 (m, 8H, morpholine-H); 6.85 (s, 1H, Ar—H), 7.05 (d, 1H, Ar—H); 7.12 (d, 1H, Ar—H).

TABLE 29

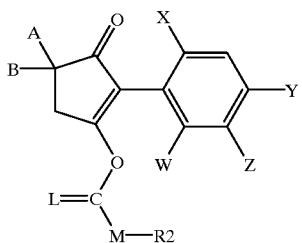

(Ic)

| Ex. No. | W | X | Y | Z | A | B | L | M | R$^2$ | m.p. °C. |
|---|---|---|---|---|---|---|---|---|---|---|
| Ic-2 | CH$_3$ | H | H | CF$_3$ | —(CH$_2$)$_5$— | | O | S | i-C$_3$H$_7$— | 106–109 |
| Ic-3 | H | CH$_3$ | H | CH$_3$ | —(CH$_2$)$_2$—CHCH$_3$—(CH$_2$)$_2$— | | O | S | i-C$_3$H$_7$— | oil |
| Ic-4 | H | CH$_3$ | H | CH$_3$ | —(CH$_2$)$_3$—CHCH$_3$—CH$_2$— | | O | S | i-C$_3$H$_7$— | oil |
| Ic-5 | CH$_3$ | CH$_3$ | CH$_3$ | CH$_3$ | —(CH$_2$)$_2$—CHOCH$_3$—(CH$_2$)$_2$— | | O | O | i-C$_4$H$_9$— | 114–116 |

Example (II-1)

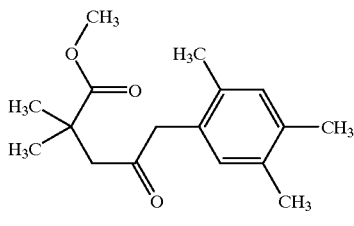

Example XII-1

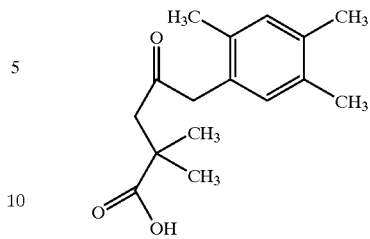

6.40 g (46.5 mmol) of potassium carbonate and 19.78 g (139.5 mmol) of methyl iodide are added to 12.2 g (46.5 mmol) of the compound of Example (XIII-1) (crude product) in 100 ml of absolute acetone, and the mixture is stirred under reflux for 16 hours. The mixture is filtered and the filtrate is concentrated under reduced pressure. The residue (11.9 g) is chromatographed over silica gel and methylene chloride/petroleum ether 8/1 to 1/0.

Yield: 4.70 g (47% of theory), oil $^1$H NMR (400 MHz, CDCl$_3$): 1.1 (s, 6H, C(CH$_3$)$_2$); 2.1 (s, 3H, ArCH$_3$); 2.2 (s, 6H, 2×ArCH$_3$); 2.7 (s, 2H, CH(CMe$_2$); 3.5 (s, 2H, ArCH$_2$), 3.6 (s, 3H, OCH$_3$); 6.8/6.9 (s, 2H, 2×ArCH).

Analogously to Example (II-1), and/or in accordance with the general preparation procedures, the compounds of the formula (II) listed in Table 30 were prepared.

A solution of 10.3 g (54 mmol; 1 eq) of methyl 2,4,5-trimethyl-phenylacetate and 20 ml of tetrahydrofuran (THF) p.a. is added dropwise, at −15° C., to a solution of 30.0 ml of LDA (lithium diisopropylamide) solution (2 molar; 1.1 eq) in 60 ml of THF p.a, and the mixture is stirred at this temperature for 30 min.

At −15° C., a solution of 4.62 g (36 mmol; 0.66 eq) of 2,2-dimethylsuccinic anhydride in 20 ml of THF p.a is then added dropwise.

The mixture is stirred at room temperature for two hours, after which 75 ml of water and 20 g of ammonium chloride are added.

The intermediate is extracted with ether and the solvents are removed under reduced pressure. The residue is boiled under reflux with 50 g of KOH and 165 ml of water for two days.

TABLE 30

(II)

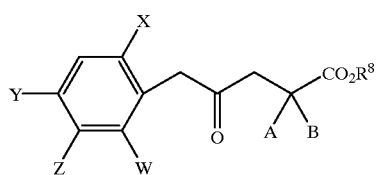

Table 30, Examples II

| Ex. No. | W | X | Y | Z | A B | R8 | m.p. ° C. |
|---|---|---|---|---|---|---|---|
| II-2 | H | CH$_3$ | H | CH$_3$ | —(CH$_2$)$_5$— | CH$_3$ | oil |
| II-3 | H | CH$_3$ | CH$_3$ | CH$_3$ | —(CH$_2$)$_5$— | CH$_3$ | oil |
| II-4 | CH$_3$ | CH$_3$ | CH$_3$ | CH$_3$ | —(CH$_2$)$_5$— | CH$_3$ | 85–86 |
| II-5 | H | CH$_3$ | CH$_3$ | CH$_3$ | —(CH$_2$)$_2$—CHCH$_3$—(CH$_2$)$_2$— | CH$_3$ | oil |
| II-6 | H | CH$_3$ | H | CH$_3$ | —(CH$_2$)$_4$— | CH$_3$ | oil |
| II-7 | H | CH$_3$ | CH$_3$ | CH$_3$ | —(CH$_2$)$_4$— | CH$_3$ | oil |
| II-8 | H | CH$_3$ | Cl | CH$_3$ | —(CH$_2$)$_5$— | CH$_3$ | oil |
| II-9 | CH$_3$ | H | H | CF$_3$ | —(CH$_2$)$_5$— | CH$_3$ | oil |
| II-10 | H | Br | CH$_3$ | CH$_3$ | —(CH$_2$)$_2$—CHCH$_3$—(CH$_2$)$_2$— | CH$_3$ | oil |
| II-11 | H | CH$_3$ | H | CH$_3$ | —(CH$_2$)$_2$—CHCH$_3$—(CH$_2$)$_2$— | CH$_3$ | oil |
| II-12 | CH$_3$ | CH$_3$ | CH$_3$ | F | —(CH$_2$)$_2$—CHCH$_3$—(CH$_2$)$_2$— | CH$_3$ | oil |
| II-13 | H | CH$_3$ | H | CH$_3$ | —(CH$_2$)$_3$—CHCH$_3$—CH$_2$— | CH$_3$ | oil |
| II-14 | H | CH$_3$ | H | CH$_3$ | —(CH$_2$)$_2$—CHOCH$_3$—(CH$_2$)$_2$— | CH$_3$ | oil |
| II-15 | H | CH$_3$ | Cl | CH$_3$ | —(CH$_2$)$_2$—CHOCH$_3$—(CH$_2$)$_2$— | CH$_3$ | oil |
| II-16 | H | CH$_3$ | CH$_3$ | CH$_3$ | —(CH$_2$)$_2$—CHOCH$_3$—(CH$_2$)$_2$— | CH$_3$ | oil |
| II-17 | CH$_3$ | CH$_3$ | CH$_3$ | CH$_3$ | —(CH$_2$)$_2$—CHOCH$_3$—(CH$_2$)$_2$— | CH$_3$ | oil |
| II-18 | H | Br | CH$_3$ | CH$_3$ | —(CH$_2$)$_2$—O—(CH$_2$)$_2$— | CH$_3$ | oil |
| II-19 | H | Cl | H | CH$_2$CH$_3$ | —(CH$_2$)$_2$—O—(CH$_2$)$_2$— | CH$_3$ | oil |
| II-20 | H | CH$_3$ | H | CH$_3$ | —(CH$_2$)$_2$—O—(CH$_2$)$_2$— | CH$_3$ | oil |
| II-21 | CH$_3$ | CH$_3$ | CH$_3$ | CH$_3$ | —(CH$_2$)$_2$—O—(CH$_2$)$_2$— | CH$_3$ | oil |

The mixture is cooled, acidified with concentrated HCl and extracted with ether. The crude product is directly reacted further.

Yield: 12.20 g, 100.00% of theory. M.p. 112–115° C.

Analogously to Example XIII-1, and/or in accordance with the general preparation procedures, the compounds of the formula (XIII) listed in Table 31 were prepared.

TABLE 31

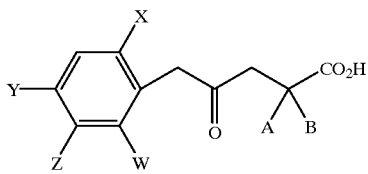

(XIII)

Table 31, Examples XIII

| Ex. No. | W | X | Y | Z | A | B | m.p. ° C. |
|---|---|---|---|---|---|---|---|
| XIII-2 | H | CH₃ | H | CH₃ | —(CH₂)₅— | | oil |
| XIII-3 | H | CH₃ | CH₃ | CH₃ | —(CH₂)₅— | | oil |
| XIII-4 | CH | CH₃ | CH₃ | CH₃ | —(CH₂)₅— | | 124–125 |
| XIII-5 | H | CH₃ | CH₃ | CH₃ | —(CH₂)₂—CHCH₃—(CH₂)₂— | | oil |
| XIII-6 | H | CH₃ | H | CH₃ | —(CH₂)₄— | | oil |
| XIII-7 | H | CH₃ | CH₃ | CH₃ | —(CH₂)₄— | | oil |
| XIII-8 | H | CH₃ | Cl | CH₃ | —(CH₂)₅— | | oil |
| XIII-9 | CH | H | H | CF₃ | —(CH₂)₅— | | oil |
| XIII-10 | H | Br | CH₃ | CH₃ | —(CH₂)₂—CHCH₃—(CH₂)₂— | | oil |
| XIII-11 | H | CH₃ | H | CH₃ | —(CH₂)₂—CHCH₃—(CH₂)₂— | | oil |
| XIII-12 | CH | CH₃ | CH₃ | F | —(CH₂)₂—CHCH₃—(CH₂)₂— | | oil |
| XIII-13 | H | CH₃ | H | CH₃ | —(CH₂)₃—CHCH₃—CH₂— | | oil |
| XIII-14 | H | CH₃ | H | CH₃ | —(CH₂)₂—CHOCH₃—(CH₂)₂— | | oil |
| XIII-15 | H | CH₃ | Cl | CH₃ | —(CH₂)₂—CHOCH₃—(CH₂)₂— | | oil |
| XIII-16 | H | CH₃ | CH₃ | CH₃ | —(CH₂)₂—CHOCH₃—(CH₂)₂— | | oil |
| XIII-17 | CH | CH₃ | CH₃ | CH₃ | —(CH₂)₂—CHOCH₃—(CH₂)₂— | | oil |
| XIII-18 | H | Br | CH₃ | CH₃ | —(CH₂)₂—O—(CH₂)₂— | | oil |
| XIII-19 | H | Cl | H | CH₂CH | —(CH₂)₂—O—(CH₂)₂— | | oil |
| XIII-20 | H | CH₃ | H | CH₃ | —(CH₂)₂—O—(CH₂)₂— | | oil |
| XIII-21 | CH | CH₃ | CH₃ | CH₃ | —(CH₂)₂—O—(CH₂)₂— | | oil |

Example (XIV-1)

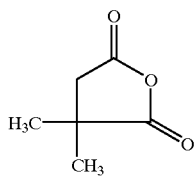

50.0 g (0.342 mol) of 2,2-dimethylsuccinic acid are boiled under reflux in 250 ml of acetic anhydride overnight.

The mixture is filtered, concentrated using a rotary evaporator and cool-distilled twice with toluene. The residue is dissolved in a little methylene chloride, admixed with n-hexane, stored overnight in an ice fridge, filtered off with suction and dried.

Yield: 36.40 g (83.00% of theory), oil.

$^1$H NMR (CDCl$_3$, 500 Mhz): 1.5 (s, 6H, CH$_3$), 2.9 (s, 2H, CH$_2$).

Example 1

Nephotettix Test

Solvent: 7 parts by weight of dimethylformamide
Emulsifier: 1 part by weight of alkylaryl polyglycol ether To produce a suitable preparation of active compound 1 part by weight of active compound is mixed with the stated amount of solvent and the stated amount of emulsifier, and the concentrate is diluted with water to the desired concentration.

Rice seedlings (*Oryzae sativa*) are treated by being dipped into the preparation of active compound of the desired concentration and are populated with the green rice leaf hopper (*Nephotettix cincticeps*) while the leaves are still moist.

After the desired period of time, the kill in % is determined. 100% means that all leaf hoppers have been killed; 0% means that none of the leaf hoppers have been killed.

In this test, for example, the compounds of Preparation Examples Ia-2, Ia-3, Ia-4, Ia-5, Ib-1, Ib-2, Ib-3, Ib-4, Ib-5, Ib-8, I-9 and Ic-1 effect, at an exemplary active compound concentration of 0.1%, a kill of 100% after 6 days.

Example 2

Phaedon Larvae Test

Solvent: 7 parts by weight of dimethylformamide
Emulsifier 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are populated with caterpillars of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, for example, the compounds of Preparation Examples Ia-1, Ib-2, Ib-4, Ib-5 and Ib-9 effect, at an exemplary active compound concentration of 0.1%, a kill of 100% after 7 days.

Example 3

Tetranychus Test (OP-resistant/dip Treatment)

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are heavily infested by all stages of the greenhouse red spider mite *Tetranychus urticae* are dipped into a preparation of active compound of the desired concentration.

After the desired period of time, the effect in % is determined. 100% means that all spider mites have been killed, 0% means that none of the spider mites have been killed.

In this test, for example, the compounds of Preparation Examples Ia-2, Ia-3, Ib-1, Ib-2, Ib-3, Ib-4, Ib-5, Ib-8 and Ic-1 had, at an exemplary active compound concentration of 0.01%, an effect of 100% after 7 days.

Example 4

Test With *Boophilus nicroplus* Resistant/SP-resistant Parkhurst Strain

Test animals: Adult females which have sucked themselves full

Solvent:: Dimethyl sulphoxide 20 mg of active compound are dissolved in 1 ml of dimethyl sulphoxide, lower concentrations are prepared by dilution with the same solvent.

The test is carried out in 5 replications. 1 µl of the solution is injected into the abdomen and the animals are transferred into dishes and kept in a controlled-environment chamber. The activity is determined via the inhibition of the position. 100% means that no tick has deposited any eggs.

In this test, for example, the compounds of Preparation Examples Ia-2 and Ia-3 had, at an exemplary active compound concentration of 20 µg/animal, an effect of in each case 100%.

What is claimed is:
1. A compound of the formula (I)

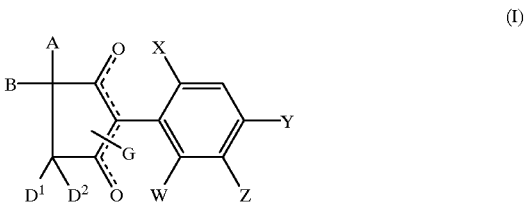

wherein
W represents hydrogen, cyano, nitro, halogen, alkyl, alkenyl, alkinyl, alkoxy, halogenalkyl and halogenalkoxy, each of which is unsubstituted or substituted by phenyl, phenoxy, phenylthio, phenylalkoxy or phenylalkylthio, X represents hydrogen, halogen, alkyl, alkenyl, alkinyl, alkoxy, halogenalkyl, halogenoalkoxy, cyano and nitro, each of which is unsubstituted or substituted by phenyl, phenylalkyl, phenoxy, phenylthio, phenylalkyloxy or phenylalkylthio, wherein at least one of the substituents of W and X does not represent hydrogen, Y represents hydrogen, halogen, alkyl, alkoxy, halogenoalkyl, halogenoalkoxy, cyano or nitro, Z represents halogen, alkyl, alkoxy, halogenoalkyl, halogenoalkoxy, hydroxyl, cyano, nitro or unsubstituted or substituted phenoxy, phenylthio, phenylalkyloxy or phenylalkylthio, or Y and Z together with the carbon atoms to which they are attached represent an unsubstituted or substituted ring which contains no heteroatoms, wherein X and W have the meanings mentioned above, or W and Z together with the carbon atoms to which they are attached represent an unsubstituted or substituted ring which contains no heteroatoms, wherein X and Y have the meanings mentioned above, A represents hydrogen or represents alkyl, alkenyl, alkinyl, alkoxyalkyl, polyalkoxyalkyl or alkylthioalkyl, each of which is unsubstituted or mono- or polysubstituted by identical or different halogens, or represents saturated or unsaturated, unsubstituted or substituted cycloalkyl or represents phenyl or phenylalkyl, each of which is unsubstituted or mono- or polysubstituted by identical or different substituents from the group consisting of halogen, alkyl, halogenoalkyl, alkoxy, halogenoalkoxy, cyano and nitro, B represents alkyl or alkoxyalkyl,
or
A and B together with the carbon atom to which they are attached form a saturated or unsaturated, unsubstituted or substituted ring which is optionally interrupted by one or more heteroatoms,
or
A and B together with the carbon atom to which they are attached form a ring where two substituents together with the carbon atoms to which they are attached form a saturated or unsaturated ring which is unsubstituted or mono- or polysubstituted by identical or different substituents from the group consisting of halogen, alkyl and alkoxy and which may contain oxygen or sulphur, $D^1$ and $D^2$ independently of one another each represent hydrogen, halogen, unsubstituted or halogen-substituted alkyl or unsubstituted or substituted phenyl, G represents hydrogen (a) or represents

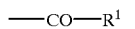
(b)

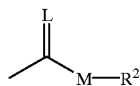
(c)

—SO$_2$—R$^3$
(d)

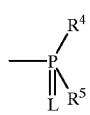
(e)

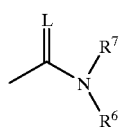  or
(f)

E
(g)

wherein
E represents a metal ion equivalent or an ammonium ion,
I represents oxygen or sulphur,
M represents oxygen or sulphur,
R$^1$ represents alkyl, alkenyl, alkoxyalkyl, alkylthioalkyl or polyalkoxyalkyl, each of which is unsubstituted or mono- or polysubstituted by identical or different halogens, or represents unsubstituted or substituted, saturated or unsaturated cycloalkyl which may be interrupted by one or more heteroatoms, or represents unsubstituted or substituted phenyl, phenylalkyl, hetaryl, or phenoxyalkyl,
R$^2$ represents alkyl, alkenyl, alkoxyalkyl, polyalkoxyalkyl, each of which is unsubstituted or mono- or polysubstituted by identical or different halogens, or represents unsubstituted or substituted cycloalkyl, phenyl or benzyl,
R$^3$ represents alkyl which is unsubstituted or mono- or polysubstituted by identical or different halogens or represents unsubstituted or substituted phenyl or phenylalkyl,
R$^4$ and R$^5$ independently of one another each represent alkyl, alkoxy, alkylamino, alkenylamino, dialkylamino, dialkenylamino, alkylthio, alkenylthio, alkinylthio, cycloalkylthio, each of which is unsubstituted or mono- or polysubstituted by identical or different halogens, or represent in each case unsubstituted or substituted phenyl, phenoxy or phenylthio,
R$^6$ and R$^7$ independently of one another each represent hydrogen, or represent alkyl, cycloalkyl, alkenyl, alkoxy, alkoxyalkyl, each of which is unsubstituted or mono- or polysubstituted by identical or different halogens, or represent unsubstituted or substituted phenyl or unsubstituted or substituted benzyl, or together with the N atom to which they are attached form an unsubstituted or substituted ring which optionally contains oxygen or sulphur,
and an enantiomerically pure form of the compound of the formula (I), provided that the following compounds are excluded: 2-(2',5'-dimethylphenyl)-4-methyl-1,3-cyclopentanedione and 2-(2',5'-dimethylphenyl)-4-methyl-5-isopentyl-1,3-cyclopentanedione.

2. The compound of claim 1 wherein
W represents hydrogen, halogen, $C_1$–$C_6$-alkyl, $C_2$–$C_6$-alkenyl or $C_2$–$C_6$-alkinyl, $C_1$–$C_6$-alkoxy, $C_1$–$C_4$-halogenoalkyl, $C_1$–$C_4$-halogenoalkoxy, nitro, cyano or unsubstituted or halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenoxy, phenylthio, phenyl-$C_1$–$C_4$-alkoxy or phenyl-$C_1$–$C_4$-alkylthio,
X represents hydrogen, halogen, $C_1$–$C_6$-alkyl, $C_2$–$C_6$-alkenyl, $C_2$–$C_6$-alkinyl, $C_1$–$C_6$-alkoxy, $C_1$–$C_4$-halogenoalkyl, $C_1$–$C_4$-halogenoalkoxy, cyano, nitro or unsubstituted or halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl, phenyl-$C_1$–$C_4$-alkyl, phenoxy, phenylthio, phenyl-$C_1$–$C_4$-alkoxy or phenyl-$C_1$–$C_4$-alkylthio, wherein at least one of the substituents of W and X does not represent hydrogen,
Y represents hydrogen, halogen, $C_1$–$C_6$-alkyl, $C_1$–$C_6$-alkoxy, $C_1$–$C_4$-halogenoalkyl, $C_1$–$C_4$-halogenoalkoxy, cyano or nitro,
Z represents halogen, $C_1$–$C_6$-alkyl, $C_1$–$C_6$-alkoxy, $C_1$–$C_4$-halogenoalkyl, $C_1$–$C_4$-halogenoalkoxy, hydroxyl, cyano, nitro or unsubstituted or halogen-, $C_1$–$C_4$-alkyl-, $C_1$–$C_4$-alkoxy-, $C_1$–$C_4$-halogenoalkyl-, $C_1$–$C_4$-halogenoalkoxy-, nitro- or cyano- substituted phenoxy, phenylthio, phenyl-$C_1$–$C_4$-alkyloxy or phenyl-$C_1$–$C_4$-alkylthio, or
Y and Z together represent unsubstituted or halogen-, $C_1$–$C_6$-alkyl-, $C_1$–$C_6$-alkoxy- or $C_1$–$C_4$-halogenoalkyl-substituted $C_3$–$C_5$-alkanediyl or $C_3$–$C_5$-alkenediyl, where X and W have the meanings mentioned above, or
W and Z together represent unsubstituted or halogen-, $C_1$–$C_6$-alkyl-, $C$,–$C_6$-alkoxy- or $C_1$–$C_4$-halogenoalkyl-substituted $C_3$–$C_5$-alkanediyl or $C_3$–$C_5$-alkenediyl, where X and Y have the meanings mentioned above,
A represents hydrogen, represents unsubstituted or halogen-substituted $C_1$–$C_{12}$-alkyl, $C_3$–$C_8$-alkenyl, $C_1$–$C_{10}$-alkoxy-$C_1$–$C_8$-alkyl, poly-$C_1$–$C_8$-alkoxy-$C_1$–$C_8$-alkyl or $C_1$–$C_{10}$-alkylthio-$C_1$–$C_6$-alkyl, or represents unsubstituted or halogen-, $C_1$–$C_6$-alkyl- or $C_1$–$C_6$-alkoxy-substituted $C_3$–$C_8$-cycloalkyl or represents unsubstituted or halogen-, $C_1$–$C_6$-alkyl, $C_1$–$C_6$-halogenoalkyl-, $C_1$–$C_6$-alkoxy-, $C_1$–$C_6$-halogenoalkoxy-, cyano- or nitro-substituted phenyl or phenyl-$C_1$–$C_6$-alkyl,
B represents $C_1$–$C_{12}$-alkyl or $C_1$–$C_8$-alkoxy-$C_1$–$C_6$-alkyl or
A and B together with the carbon atom to which they are attached represent $C_3$–$C_{10}$-cycloalkyl or $C_5$–$C_{10}$-cycloalkenyl in which optionally one methylene group is replaced by oxygen or sulphur and which are unsubstituted or substituted by $C_1$–$C_8$-alkyl, $C_3$–$C_{10}$-cycloalkyl, $C_1$–$C_8$-halogenoalkyl, $C_1$–$C_8$-alkoxy, $C_1$–$C_8$-alkylthio, halogen or phenyl, or
A and B together with the carbon atom to which they are attached represent $C_5$–$C_8$-cycloalkyl which is unsubstituted or substituted by an alkylenedioxyl or by an alkylenedithioyl or by an alkylenediyl group which optionally contains one or two not directly adjacent oxygen and/or sulphur atoms and which, with the carbon atom to which it is attached, forms a further five- to eight-membered ring, or A and B together with the carbon atom to which they are attached represent $C_3$–$C_8$-cycloalkyl or $C_5$–$C_8$-cycloalkenyl in which two carbon atoms are linked with one another by $C_3$–$C_6$-alkanediyl, $C_3$–$C_6$-alkenediyl or $C_4$–$C_6$-alkanediendiyl, each of which is unsubstituted or substituted by $C_1$–$C_6$-alkyl, $C_1$–$C_6$-alkoxy or halogen, in which in each case optionally one methylene group is replaced by oxygen or sulphur, $D^1$ and $D^2$ independently of one another each represent hydrogen, halogen, $C_1$–$C_6$-alkyl which is optionally mono- or polysubstituted by identical or different halogens or represent phenyl which is unsubstituted or mono- or polysubstituted by identical or different substituents from the group consisting of halogen, $C_1$–$C_6$-alkyl, $C_1$–$C_6$-alkoxy, nitro, $C_1$–$C_6$-halogenoalkyl or $C_1$–$C_6$-halogenoalkoxy, G represents hydrogen (a) or represents

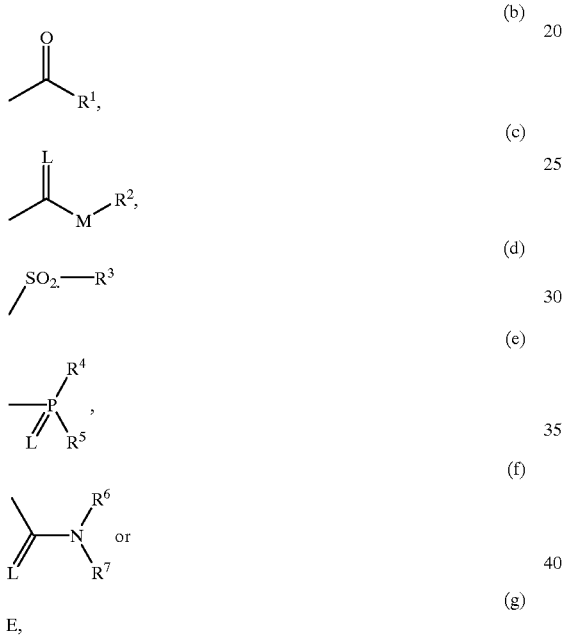

E, wherein
E represents a metal ion equivalent or an ammonium ion,
L represents oxygen or sulphur and
M represents oxygen or sulphur,
$R^1$ represents unsubstituted or halogen-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl or poly-$C_1$–$C_8$-alkoxy-$C_1$–$C_8$-alkyl or represents unsubstituted or halogen-, $C_1$–$C_6$-alkyl- or $C_1$–$C_6$-alkoxy-substituted $C_3$–$C_8$-cycloalkyl in which optionally one or two not directly adjacent methylene groups are replaced by oxygen and/or sulphur, or represents unsubstituted or halogen-, cyano-, nitro-, $C_1$–$C_6$-alkyl-, $C_1$–$C_6$-alkoxy-, $C_1$–$C_6$-halogenoalkyl-, $C_1$–$C_6$-halogenoalkoxy-, $C_1$–$C_6$-alkylthio- or $C_1$–$C_6$-alkylsulphonyl-substituted phenyl, or represents unsubstituted or halogen-, nitro, cyano, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl, or represents unsubstituted or halogen- or $C_1$–$C_6$-alkyl-substituted 5- or 6-membered hetaryl having one or two heteroatoms from the group consisting of oxygen, sulphur and nitrogen, or represents unsubstituted or halogen- or $C_1$–$C_6$-alkyl-substituted phenoxy-$C_1$–$C_6$-alkyl, $R^2$ represents unsubstituted or halogen-substituted $C_1$–$C_{20}$-alkyl, $C_2$–$C_{20}$-alkenyl, $C_1$–$C_8$-alkoxy-$C_2$–$C_8$-alkyl or poly-$C_1$–$C_8$-alkoxy-$C_2$–$C_8$-alkyl, represents unsubstituted or halogen-, $C_1$–$C_6$-alkyl- or $C_1$–$C_6$-alkoxy-substituted $C_3$–$C_8$-cycloalkyl or represents unsubstituted or halogen-, cyano-, nitro-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl or benzyl, $R^3$ represents unsubstituted or halogen-substituted $C_1$–$C_8$-alkyl or unsubstituted or halogen-, $C_1$–$C_6$-alkyl-, $C_1$–$C_6$-alkoxy-, $C_1$–$C_4$-halogeno-alkyl-, $C_1$–$C_4$-halogenoalkoxy-, cyano- or nitro-substituted phenyl or benzyl, $R^4$ and $R^5$ independently of one another each represent in each case unsubstituted or halogen-substituted $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio or $C_3$–$C_8$-alkenylthio or represent in each case unsubstituted or halogen-, nitro-, cyano-, $C_1$–$C_4$-alkoxy-, $C_1$–$C_4$-halogenoalkoxy-, $C_1$–$C_4$-alkylthio-, $C_1$–$C_4$-halogenoalkylthio, $C_1$–$C_4$-alkyl- or $C_1$–$C_4$-halogenoalkyl-substituted phenyl, phenoxy or phenylthio and $R^6$ and $R^7$ independently of one another each represent hydrogen, or represent unsubstituted or halogen-substituted $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_2$–$C_8$-alkyl, or represent unsubstituted or halogen-, $C_1$–$C_8$-alkyl-, $C_1$–$C_8$-halogenoalkyl- or $C_1$–$C_8$-alkoxy-substituted phenyl or benzyl or together represent an unsubstituted or $C_1$–$C_6$-alkyl-substituted $C_3$–$C_6$-alkylene radical in which optionally one methylene group is replaced by oxygen or sulphur, provided that the following compound is excluded: 2-(2',5'-dimethylphenyl)-4-methyl-1,3-cyclopentanedione.

3. The compound of claim 1 wherein
W represents hydrogen, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro, cyano or unsubstituted or fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy-, nitro- or cyano-substituted phenyl, phenoxy or benzyloxy, X represents hydrogen, fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, cyano, nitro or unsubstituted or fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy-, nitro- or cyano-substituted phenyl, phenoxy, benzyl or benzyloxy, wherein at least one of the substituents of W and X does not represent hydrogen, Y represents hydrogen, fluorine, chlorine, bromine $C_1$–$C_4$-alkyl, $C_1$–$C_4$-alkoxy, $C_1$–$C_2$-halogenoalkyl, $C_1$–$C_2$-halogenoalkoxy, cyano or nitro, Z represents fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, hydroxyl, cyano or nitro or unsubstituted or fluorine-, chlorine-, bromine-, $C_1$–$C_4$-alkyl-, $C_1$–$C_4$-alkoxy-, $C_1$–$C_2$-halogenoalkyl-, $C_1$–$C_2$-halogenoalkoxy-, nitro- or cyano-substituted phenoxy or benzyloxy, or Y and Z together represent unsubstituted or fluorine-, chlorine-, bromine-, $C_1$–$C_4$-alkyl-, $C_1$–$C_4$-alkoxy- or $C_1$–$C_2$-halogenoalkyl-substituted $C_3$–$C_4$-alkanediyl or represent $C_3$–$C_4$-alkenediyl, wherein X and W have the meanings mentioned above, or W and Z together represent unsubstituted or fluorine-, chlorine-, bromine-, $C_1$–$C_4$-alkyl-, $C_1$–$C_4$-alkoxy- or $C_1$–$C_2$-halogenoalkyl-substituted $C_3$–$C_4$-alkanediyl or represent $C_3$–$C_4$-alkenediyl, wherein X and Y have the meanings mentioned above, A represents hydrogen, represents unsubstituted or fluorine- or chlorine-substituted $C_1$–$C_{10}$-alkyl, $C_3$–$C_6$-alkenyl, $C_1$–$C_8$-alkoxy-$C_1$–$C_6$-alkyl, poly-$C_1$–$C_6$-alkoxy-$C_1$–$C_6$-alkyl or $C_1$–$C_8$-alkylthio-$C_1$–$C_6$-alkyl or represent unsubstituted or fluorine-, chlorine-, $C_1$–$C_4$-alkyl- or $C_1$–$C_4$-alkoxy-substituted $C_3$–$C_7$-cycloalkyl or represents unsubstituted or fluorine-, chlorine-, bromine-, $C_1$–$C_4$-alkyl-, $C_1$–$C_4$-halogenoalkyl-, $C_1$–$C_4$-alkoxy-, $C_1$–$C_4$-halogenoalkoxy-, cyano- or nitro-substituted phenyl or phenyl-$C_1$–$C_4$-alkyl, B represents $C_1$–$C_{10}$-alkyl or $C_1$–$C_6$-alkoxy-$C_1$–$C_4$-alkyl or A and B together with the carbon atom to which they are attached represent $C_3$–$C_8$-cycloalkyl or $C_5$–$C_8$-cycloalkenyl in which in each case optionally one methylene group is replaced by oxygen or sulphur and which are unsubstituted or substituted by $C_1$–$C_6$-alkyl, $C_3$–$C_8$-cycloalkyl, $C_1$–$C_3$-halogenoalkyl, $C_1$–$C_6$-alkoxy, $C_1$–$C_6$-alkylthio, fluorine, chlorine or phenyl, or A and B together with the carbon atom to which they are attached represent $C_5$–$C_8$-cycloalkyl which is substituted by an alkylenedioxyl or by an alkylenedithio group or by an alkylenediyl group which optionally contains one or two not directly adjacent oxygen or sulphur atoms which, with the carbon atom to which it is attached, forms a further five- to seven-membered ring, or A and B together with the carbon atom to which they are attached represent $C_3$–$C_6$-cycloalkyl or $C_5$–$C_6$-cycloalkenyl in which two carbon atoms are linked by unsubstituted or $C_1$–$C_4$-alkyl-, $C_1$–$C_4$-alkoxy-, fluorine-, chlorine- or bromine-substituted $C_3$–$C_5$-alkanediyl, $C_3$–$C_5$-alkenediyl, where in each case optionally one methylene group is replaced by oxygen or sulphur, or by butadienediyl, $D^1$ and $D^2$ independently of one another each represent hydrogen or represent $C_1$–$C_4$-alkyl which is unsubstituted or mono- to pentasubstituted by identical or different substituents from the group consisting of fluorine and chlorine, G represents hydrogen (a) or represents one of the groups

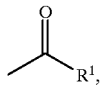

(b)

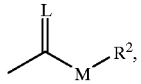

(c)

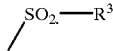

(d)

-continued

(e)

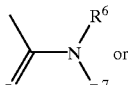

(f)

E, (g)

wherein
E represents a metal ion equivalent or an ammonium ion,
L represents oxygen or sulphur and
M represents oxygen or sulphur, $R^1$ represents unsubstituted or fluorine- or chlorine-substituted $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl or poly-$C_1$–$C_6$-alkoxy-$C_1$–$C_6$-alkyl or represents unsubstituted or fluorine-, chlorine- $C_1$–$C_5$-alkyl- or $C_1$–$C_5$-alkoxy-substituted $C_3$–$C_7$-cycloalkyl in which optionally one or two not directly adjacent methylene groups are replaced by oxygen and/or sulphur, or represents unsubstituted or fluorine-, chlorine-, bromine-, cyano-, nitro-, $C_1$–$C_4$-alkyl-, $C_1$–$C_4$-alkoxy-, $C_1$–$C_3$-halogenoalkyl-, $C_1$–$C_3$-halogenoalkoxy-, $C_1$–$C_4$-alkylthio- or $C_1$–$C_4$-alkylsulphonyl-substituted phenyl, or represents unsubstituted or fluorine-, chlorine-, bromine-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl-$C_1$–$C_4$-alkyl, or represents unsubstituted or fluorine-, chlorine- bromine- or $C_1$–$C_4$-alkyl-substituted pyrazolyl, thiazolyl, pyridyl, pyrimidyl, furanyl or thienyl, or represents unsubstituted or fluorine-, chlorine-, bromine- or $C_1$–$C_4$-alkyl-substituted phenoxy-$C_1$–$C_5$-alkyl, $R^2$ represents unsubstituted or fluorine- or chlorine-substituted $C_1$–$C_{16}$-alkyl, $C_2$–$c_{16}$-alkenyl, $C_1$–$C_6$-alkoxy-$C_2$–$C_6$-alkyl or poly-$C_1$–$C_6$-alkoxy-$C_2$–$C_6$-alkyl, or represents unsubstituted or fluorine-, chlorine-, $C_1$–$C_4$-alkyl- or $C_1$–$C_4$alkoxy-substituted $C_3$–$C_7$-cycloalkyl or represents unsubstituted or fluorine-, chlorine, bromine-, cyano-, nitro-, $C_1$–$C_4$-alkyl-, $C_1$–$C_3$-alkoxy-, $C_1$–$C_3$-halogenoalkyl- or $C_1$–$C_3$-halogenoalkoxy-substituted phenyl or benzyl, $R^3$ represents unsubstituted or fluorine- or chlorine-substituted $C_1$–$C_6$-alkyl or represents unsubstituted or fluorine-, chlorine-, bromine-, $C_1$–$C_4$-alkyl-, $C_1$–$C_4$-alkoxy-, $C_1$–$C_2$-halogenoalkoxy-, $C_1$–$C_2$-halogenoalkyl-, cyano or nitro-substituted phenyl or benzyl, $R^4$ and $R^5$ independently of one another each represent in each case unsubstituted or fluorine- or chlorine-substituted $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio or $C_3$–$C_4$-alkenylthio or represent unsubstituted or fluorine-, chlorine-, bromine-, nitro-, cyano-, $C_1$–$C_3$-alkoxy-, $C_1$–$C_3$-halogenoalkoxy-, $C_1$–$C_3$-alkylthio-, $C_1$–$C_3$-halogenoalkylthio-, $C_1$–$C_3$-alkyl- or $C_1$–$C_3$-halogenoalkyl-substituted phenyl, phenoxy or phenylthio and $R^6$ and $R^7$ independently of one another each represent hydrogen, or represent unsubstituted or fluorine- or chlorine-substituted $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, or represent unsubstituted or fluorine-, chlorine-, bromine-, $C_1$–$C_5$-halogenoalkyl-, $C_1$–$C_5$-alkyl- or $C_1$–$C_5$-alkoxy-substituted phenyl or benzyl, or together represent an unsubstituted or $C_1$–$C_4$-alkyl-substituted $C_3$–$C_6$-alkylene radical in which optionally one methylene group is replaced by oxygen or sulphur, provided that the following compound is excluded: 2-(2',5'-dimethylphenyl)-4-methyl-1,3-cyclopentanedione.

4. The compound of claim 1, wherein

W represents hydrogen, fluorine, chlorine, bromine, methyl, ethyl, n-propyl, n-butyl, iso-propyl, iso-butyl, tert-butyl, methoxy, ethoxy, n-propoxy, iso-propoxy, trifluoromethyl, difluoromethoxy, trifluoromethoxy, cyano, nitro, phenyl or benzyloxy, X represents hydrogen, fluorine, chlorine, bromine, methyl, ethyl, n-propyl, n-butyl, iso-butyl, iso-propyl, tert-butyl, methoxy, ethoxy, n-propoxy, iso-propoxy, trifluoromethyl, trifluoromethoxy, difluoromethoxy, cyano, nitro, phenyl or benzyloxy, wherein at least one of the substituents of W and X does not represent hydrogen, Y represents hydrogen, fluorine, chlorine, bromine, methyl, ethyl, n-propyl, iso-propyl, n-butyl, iso-butyl, tert-butyl, methoxy, ethoxy, n-propoxy, iso-propoxy, trifluoromethyl, trifluoromethoxy, difluoromethoxy, cyano or nitro, Z represents fluorine, chlorine, bromine, methyl, ethyl, n-propyl, n-butyl, iso-butyl, iso-propyl, tert-butyl, methoxy, ethoxy, n-propoxy, iso-propoxy, trifluoromethyl, trifluoromethoxy, difluoromethoxy, cyano or nitro, or Y and Z together represent unsubstituted or fluorine-, chlorine-, methyl-, ethyl-, n-propyl-, iso-propyl-, methoxy-, ethoxy-, n-propoxy-, iso-propoxy- or trifluoromethyl-substituted $C_3$–$C_4$-alkanediyl, wherein W and X have the meanings mentioned above, or W and Z together represent unsubstituted or fluorine-, chlorine-, methyl-, ethyl-, n-propyl-, iso-propyl-, methoxy-, ethoxy-, n-propoxy-, iso-propoxy- or trifluoromethyl-substituted $C_3$–$C_4$-alkanediyl, wherein X and Y have the meanings mentioned above, A represents hydrogen, or represents unsubstituted or fluorine- or chlorine-substituted $C_1$–$C_8$-alkyl, $C_3$–$C_4$-alkenyl, $C_1$–$C_6$-alkoxy-$C_1$–$C_4$-alkyl, poly-$C_1$–$C_4$-alkoxy-$C_1$–$C_4$-alkyl or $C_1$–$C_6$-alkylthio-$C_1$–$C_4$-alkyl or represents unsubstituted or fluorine-, chlorine-, methyl- or methoxy-substituted $C_3$–$C_6$-cycloalkyl or represents unsubstituted or fluorine-, chlorine-, bromine-, methyl-, ethyl-, n-propyl-, iso-propyl-, methoxy-, ethoxy-, trifluoromethyl-, trifluoromethoxy-, cyano- or nitro-substituted phenyl or benzyl, B represents $C_1$–$C_8$-alkyl or $C_1$–$C_4$-alkoxy-$C_1$–$C_2$-alkyl or A and B together with the carbon atom to which they are attached represent $C_3$–$C_8$-cycloalkyl or $C_5$–$C_8$-cycloalkenyl in which in each case optionally one methylene group is replaced by oxygen or sulphur and which are unsubstituted or substituted by methyl, ethyl, n-propyl, iso-propyl, n-butyl, iso-butyl, sec-butyl, tert-butyl, cyclohexyl, trifluoromethyl, methoxy, ethoxy, n-propoxy, iso-propoxy, n-butoxy, iso-butoxy, sec-butoxy, tert-butoxy, methylthio, ethylthio, fluorine, chlorine or phenyl, $D^1$ and $D^2$ independently of one another each represent hydrogen, methyl or ethyl, G represents hydrogen (a) or

(b)

(c)

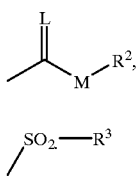

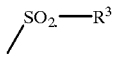

(d)

(e)

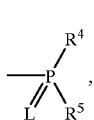

(f)

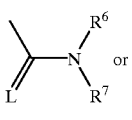

or (g)

E, wherein

E represents a metal ion equivalent or an ammonium ion,

L represents oxygen or sulphur and

M represents oxygen or sulphur, $R^1$ represents unsubstituted or fluorine- or chlorine-substituted $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl or poly-$C_1$–$C_4$-alkoxy-$C_1$–$C_4$-alkyl or represents unsubstituted or fluorine-, chlorine-, methyl-, ethyl-, n-propyl-, i-propyl-, n-butyl-, i-butyl-, tert-butyl-, methoxy-, ethoxy-, n-propoxy- or iso-propoxy-substituted $C_3$-$C_6$-cycloalkyl in which optionally one or two not directly adjacent methylene groups are replaced by oxygen and/or sulphur, or represents unsubstituted or fluorine-, chlorine-, bromine-, cyano-, nitro-, methyl-, ethyl-, n-propyl-, i-propyl-, methoxy-, ethoxy-, trifluoromethyl-, trifluoromethoxy-, methylthio-, ethylthio-, methylsulphonyl- or ethylsulphonyl-substituted phenyl, or represents unsubstituted or fluorine-, chlorine-, bromine-, methyl-, ethyl-, n-propyl-, i-propyl-, methoxy-, ethoxy-, trifluoromethyl- or trifluoromethoxy-substituted benzyl, or represents unsubstituted or fluorine-, chlorine-, bromine-, methyl- or ethyl-substituted furanyl, thienyl or pyridyl, or represents unsubstituted or fluorine-, chlorine-, methyl- or ethyl-substituted phenoxy-$C_1$–$C_4$-alkyl, $R^2$ represents unsubstituted or fluorine- or chlorine-substituted $C_1$–$C_{14}$-alkyl, $C_2$–$C_{14}$-alkenyl, $C_1$–$C_4$-alkoxy-$C_2$–$C_6$-alkyl or poly-$C_1$–$C_4$-alkoxy-$C_2$–$C_6$-alkyl, or represents unsubstituted or fluorine-, chlorine-, methyl-, ethyl-, n-propyl-, iso-propyl- or methoxy-substituted $C_3$–$C_6$-cycloalkyl, or represents unsubstituted or fluorine-, chlorine-, cyano- nitro-, methyl-, ethyl-, n-propyl-, i-propyl-, methoxy-, ethoxy-, trifluoromethyl- or trifluoromethoxy-substituted phenyl or benzyl, R³ represents unsubstituted or fluorine-, or chlorine-substituted methyl, ethyl, n-propyl, iso-propyl, n-butyl, tert-butyl or unsubstituted or fluorine-, chlorine-, bromine-, methyl-, ethyl-, iso-propyl-, tert-butyl-, methoxy-, ethoxy-, iso-propoxy-, trifluoromethyl-, trifluoromethoxy-, cyano- or nitro-substituted phenyl or benzyl, R⁴ and R⁵ independently of one another each represent unsubstituted or fluorine- or chlorine-substituted $C_1$–$C_4$-alkyl, $C_1$–$C_4$-alkoxy, $C_1$–$C_4$-alkylamino, di-($C_1$–$C_4$-alkyl)amino or $C_1$–$C_4$-alkylthio or represent unsubstituted or fluorine-, chlorine-, bromine-, nitro-, cyano-, methyl-, methoxy-, trifluoromethyl- or trifluoromethoxy-substituted phenyl, phenoxy or phenylthio and R⁶ and R⁷ independently of one another each represent hydrogen, or represent unsubstituted or fluorine- or chlorine-substituted $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_2$–$C_4$-alkyl, represent unsubstituted or fluorine-, chlorine-, bromine-, methyl-, methoxy- or trifluoromethyl-substituted phenyl or benzyl or together represent an unsubstituted or methyl- or ethyl-substituted $C_5$–$C_6$-alkylene radical in which optionally one methylene group is replaced by oxygen or sulphur, provided that the following compound is excluded: 2-(2',5'-dimethylphenyl)-4-methyl-1,3-cyclopentanedione.

5. A compound of the formula (II)

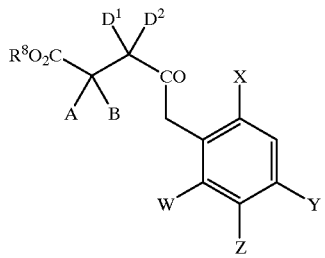

(II)

wherein

W represents hydrogen, cyano, nitro, halogen, alkyl, alkenyl, alkinyl, alkoxy, halogenalkyl and halogenalkoxy, each of which is unsubstituted or substituted by phenyl, phenoxy, phenylthio, phenylalkoxy or phenylalkylthio, X represents hydrogen, halogen, alkyl, alkenyl, alkinyl, alkoxy, halogenalkyl, halogenoalkoxy, cyano and nitro, each of which is unsubstituted or substituted by phenyl, phenylalkyl, phenoxy, phenylthio, phenylalkyloxy or phenylalkylthio, wherein at least one of the substituents of W and X does not represent hydrogen, Y represents hydrogen, halogen, alkyl, alkoxy, halogenoalkyl, halogenoalkoxy, cyano or nitro, Z represents halogen, alkyl, alkoxy, halogenoalkyl, halogenoalkoxy, hydroxyl, cyano, nitro or unsubstituted or substituted phenoxy, phenylthio, phenylalkyloxy or phenylalkylthio, or Y and Z together with the carbon atoms to which they are attached represent an unsubstituted or substituted ring which contains no heteroatoms, wherein X and W have the meanings mentioned above, or W and Z together with the carbon atoms to which they are attached represent an unsubstituted or substituted ring which contains no heteroatoms, wherein X and Y have the meanings mentioned above, A represents hydrogen or represents alkyl, alkenyl, alkinyl, alkoxyalkyl, polyalkoxyalkyl or alkylthioalkyl, each of which is unsubstituted or mono- or polysubstituted by identical or different halogens, or represents saturated or unsaturated, unsubstituted or substituted cycloalkyl or represents phenyl or phenylalkyl, each of which is unsubstituted or mono- or polysubstituted by identical or different substituents from the group consisting of halogen, alkyl, halogenoalkyl, alkoxy, halogenoalkoxy, cyano and nitro, B represents alkyl or alkoxyalkyl, or A and B together with the carbon atom to which they are attached form a saturated or unsaturated, unsubstituted or substituted ring which is optionally interrupted by one or more heteroatoms, or A and B together with the carbon atom to which they are attached form a ring where two substituents together with the carbon atoms to which they are attached form a saturated or unsaturated ring which is unsubstituted or mono- or polysubstituted by identical or different substituents from the group consisting of halogen, alkyl and alkoxy and which may contain oxygen or sulphur, D¹ and D² independently of one another each represent hydrogen, halogen, unsubstituted or halogen-substituted alkyl or unsubstituted or substituted phenyl, and R⁸ represents alkyl.

6. A compound of the formula (XIII)

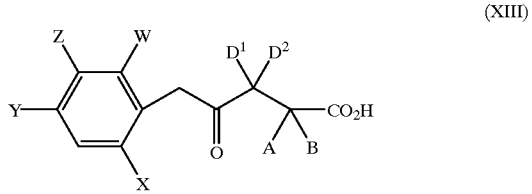

(XIII)

wherein

W represents hydrogen, cyano, nitro, halogen, alkyl, alkenyl, alkinyl, alkoxy, halogenalkyl and halogenalkoxy, each of which is unsubstituted or substituted by phenyl, phenoxy, phenylthio, phenylalkoxy or phenylalkylthio, X represents hydrogen, halogen, alkyl, alkenyl, alkinyl, alkoxy, halogenalkyl, halogenoalkoxy, cyano and nitro, each of which is unsubstituted or substituted by phenyl, phenylalkyl, phenoxy, phenylthio, phenylalkyloxy or phenylalkylthio, wherein at least one of the substituents of W and X does not represent hydrogen, Y represents hydrogen, halogen, alkyl, alkoxy, halogenoalkyl, halogenoalkoxy, cyano or nitro, Z represents halogen, alkyl, alkoxy, halogenoalkyl, halogenoalkoxy, hydroxyl, cyano, nitro or unsubstituted or substituted phenoxy, phenylthio, phenylalkyloxy or phenylalkylthio, or Y and Z together with the carbon atoms to which they are attached represent an unsubstituted or substituted ring which contains no heteroatoms, wherein X and W have the meanings mentioned above, or W and Z together with the carbon atoms to which they are attached represent an unsubstituted or substituted ring which contains no heteroatoms, wherein X and Y have the meanings mentioned above, A represents hydrogen or represents alkyl, alkenyl, alkinyl, alkoxyalkyl, polyalkoxyalkyl or alkylthioalkyl, each of which is unsubstituted or mono- or polysubstituted by identical or different halogens, or represents saturated or unsaturated, unsubstituted or substituted cycloalkyl or represents phenyl or phenylalkyl, each of which is unsubstituted or mono- or polysubstituted by identical or different substituents from the group consisting of halogen, alkyl, halogenoalkyl, alkoxy, halogenoalkoxy, cyano and nitro, B represents alkyl or alkoxyalkyl, or A and B together with the carbon atom to which they are attached form a saturated or unsaturated, unsubstituted or substituted ring which is optionally interrupted by one or more heteroatoms, or A and B together with the carbon atom to which they are attached form a ring where two substituents together with the carbon atoms to which they are attached form a saturated or unsaturated ring which is unsubstituted or mono- or polysubstituted by identical or different substituents from the group consisting of halogen, alkyl and alkoxy and which may contain oxygen or sulphur, $D^1$ and $D^2$ independently of one another each represent hydrogen, halogen, unsubstituted or halogen-substituted alkyl or unsubstituted or substituted phenyl.

7. A compound of the formula (XVI)

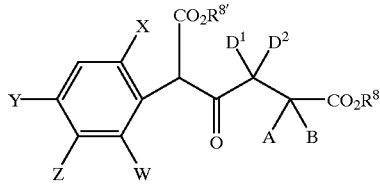

(XVI)

wherein

W represents hydrogen, cyano, nitro, halogen, alkyl, alkenyl, alkinyl, alkoxy, halogenalkyl and halogenalkoxy, each of which is unsubstituted or substituted by phenyl, phenoxy, phenylthio, phenylalkoxy or phenylalkylthio, X represents hydrogen, halogen, alkyl, alkenyl, alkinyl, alkoxy, halogenalkyl, halogenoalkoxy, cyano and nitro, each of which is unsubstituted or substituted by phenyl, phenylalkyl, phenoxy, phenylthio, phenylalkyloxy or phenylalkylthio, wherein at least one of the substituents of W and X does not represent hydrogen, Y represents hydrogen, halogen, alkyl, alkoxy, halogenoalkyl, halogenoalkoxy, cyano or nitro, Z represents halogen, alkyl, alkoxy, halogenoalkyl, halogenoalkoxy, hydroxyl, cyano, nitro or unsubstituted or substituted phenoxy, phenylthio, phenylalkyloxy or phenylalkylthio, or Y and Z together with the carbon atoms to which they are attached represent an unsubstituted or substituted ring which contains no heteroatoms, wherein X and W have the meanings mentioned above, or W and Z together with the carbon atoms to which they are attached represent an unsubstituted or substituted ring which contains no heteroatoms, wherein X and Y have the meanings mentioned above, A represents hydrogen or represents alkyl, alkenyl, alkinyl, alkoxyalkyl, polyalkoxyalkyl or alkylthioalkyl, each of which is unsubstituted or mono- or polysubstituted by identical or different halogens, or represents saturated or unsaturated, unsubstituted or substituted cycloalkyl or represents phenyl or phenylalkyl, each of which is unsubstituted or mono- or polysubstituted by identical or different substituents from the group consisting of halogen, alkyl, halogenoalkyl, alkoxy, halogenoalkoxy, cyano and nitro, B represents alkyl or alkoxyalkyl, or A and B together with the carbon atom to which they are attached form a saturated or unsaturated, unsubstituted or substituted ring which is optionally interrupted by one or more heteroatoms, or A and B together with the carbon atom to which they are attached form a ring where two substituents together with the carbon atoms to which they are attached form a saturated or unsaturated ring which is unsubstituted or mono- or polysubstituted by identical or different substituents from the group consisting of halogen, alkyl and alkoxy and which may contain oxygen or sulphur, $D^1$ and $D^2$ independently of one another each represent hydrogen, halogen, unsubstituted or halogen-substituted alkyl or unsubstituted or substituted phenyl, and $R^8$ and $R^{8'}$ each represent alkyl.

8. A process for preparing a compound of the formula (I) according to claim 1, comprising the steps of:

a) intermolecularly cyclizing a compound of the formula (II)

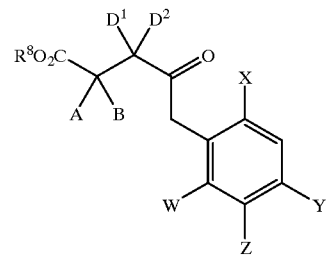

(II)

wherein

A, B, $D^1$, $D^2$, W, X, Y and Z are each as defined in claim 1, and $R^8$ represents alkyl, producing a compound of the formula (Ia)

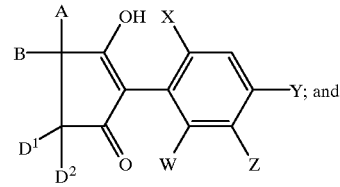

(Ia)

b) reacting the compound of the formula (Ia) with an acyl halide of the formula (III)

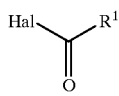 (III)

wherein
R₁ is as defined in claim 1, and
Hal represents halogen,
or
c) reacting the compound of the formula (Ia) with a carboxylic anhydride of the formula (IV)

$$R^1-CO-O-CO-R^1 \quad (IV)$$

wherein
R¹ is as defined in claim 1,
or
d) reacting the compound of the formula (Ia) with a chloroformic ester or a chloroformic thioester of the formula (V)

$$R^2-M-CO-Cl \quad (V)$$

wherein
R² and M are each as defined in claim 1,
or
e) reacting the compound of the formula (Ia) with a chloromonothioformic ester or a chlorodithioformic ester of the formula (VI)

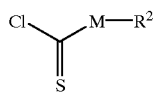 (VI)

wherein
R² and M are each as defined in claim 1,
or
f) reacting the compound of the formula (Ia) with a sulphonyl chloride of the formula (VII)

$$R^3-SO_2-Cl \quad (VII)$$

wherein
R³ is as defined in claim 1,
or
g) reacting the compound of the formula (Ia) with a phosphorus compound of the formula (VIII)

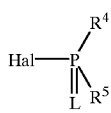 (VIII)

wherein
L, R⁴ and R⁵ are each as defined in claim 1, and
Hal represents halogen,
or
h) reacting the compound of the formula (Ia) with an isocyanate or an isothiocyanate of the formula (XI)

$$R^6-N=C=L \quad (XI)$$

wherein
R⁶ and L are each as defined in claim 1,
or
i) reacting the compound of the formula (Ia) with a carbamoyl chloride or thiocarbamoyl chloride of the formula (XII)

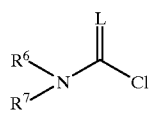 (XII)

wherein
L, R⁶ and R⁷ are each as defined in claim 1,
or
j) reacting the compound of the formula (Ia) with a metal compound of the formula (IX)

$$Me(OR^{10})_t \quad (IX)$$

wherein
Me represents a mono- or divalent metal,
t represents the number 1 or 2, and
R¹⁰ represents hydrogen or alkyl,
or
k) reacting the compound of the formula (Ia) with an amine of the formula

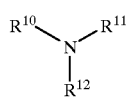 (X)

wherein
R¹⁰, R¹¹ and R¹² each represent hydrogen or alkyl.

9. The process of claim 8 wherein the reaction in step a) is carried out in the presence of a diluent and a base.

10. The process of claim 8 wherein the reaction in steps b), c), d), e), f), g), h), i), j) and k) are carried out in the presence of a diluent.

11. The process of claim 8 wherein the reaction in steps b), c), d), e), f), g) and i) are carried out in the presence of an acid binder.

12. The process of claim 8 wherein the reaction in steps b), c), d), e), f), g) and i) are carried out in the presence of a diluent and an acid binder.

13. The process of claim 8 wherein the reaction in step h) is carried out in the presence of a catalyst.

14. The process of claim 8 wherein the reaction in step h) is carried out the presence of a diluent and a catalyst.

15. A pesticide or herbicide composition comprising an effective amount of one or more compounds of claim 1 and a member selected from the group consisting of a solvent, an emulsifier, a dispresant, a binder, a water repellent, a desiccant, a UV stabilizer, a colorant and mixtures thereof.

16. A method for controlling pests and weeds, comprising the step of allowing an effective amount of one or more compound of claim 1 to act on pests or weeds and/or their habitat.

17. A process for preparing a pesticide or a herbicide comprising mixing a compound of claim 1 with a member selected from the group consisting of a solvent, an emulsifier, a dispresant, a binder, a water repellent, a desiccant, a UV stabilizer, a colorant and mixtures thereof.

* * * * *